(12) United States Patent
Taylor et al.

(10) Patent No.: US 6,572,856 B1
(45) Date of Patent: Jun. 3, 2003

(54) METHODS FOR THE PREVENTION AND TREATMENT OF CANCER USING ANTI-C3B (I) ANTIBODIES

(75) Inventors: Ronald Taylor, Charlottesville, VA (US); Alessandra Nardin, Paris (FR); William M. Sutherland, Earlysville, VA (US); Mitchell H. Sokoloff, Hinsdale, IL (US); Leland Chung, Lovingston, VA (US)

(73) Assignee: The University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/724,620

(22) Filed: Nov. 28, 2000

Related U.S. Application Data

(63) Continuation-in-part of application No. 09/392,500, filed on Sep. 9, 1999.
(60) Provisional application No. 60/099,782, filed on Sep. 10, 1998, and provisional application No. 60/123,786, filed on Mar. 11, 1999.

(51) Int. Cl.$^7$ .................. A61K 39/395; C07K 16/00; C12P 21/08

(52) U.S. Cl. ................... 424/130.1; 424/133.1; 424/136.1; 424/138.1; 424/141.1; 424/143.1; 424/152.1; 424/174.1; 530/391.3; 530/391.7; 530/387.1; 530/387.3; 530/387.7; 530/388.1; 530/388.25

(58) Field of Search .............. 530/391.3, 391.7, 530/387.1, 387.3, 387.7, 388.1, 388.25, 863, 864, 865; 424/130.1, 133.1, 136.1, 138.1, 141.1, 143.1, 152.1, 174.1

(56) References Cited

U.S. PATENT DOCUMENTS

| | | | |
|---|---|---|---|
| 5,376,356 A | | 12/1994 | Morgan, Jr. |
| 5,985,847 A | * | 11/1999 | Carson et al. |
| 6,221,621 B1 | | 4/2001 | Kinders et al. |

FOREIGN PATENT DOCUMENTS

| | | |
|---|---|---|
| EP | 0448464 | 9/1991 |
| WO | WO 87/06344 | 10/1987 |
| WO | WO 9637234 | 11/1996 |
| WO | WO 9738136 | 10/1997 |
| WO | WO 9839659 | 9/1998 |

OTHER PUBLICATIONS

Irie, Proc Am Assoc Cancer Res, 1975, vol. 16, p. 170.*
Michael et al, FASEB, 1993, vol. 7, p. A375.*
Howard and Hughes–Jones, Monoclonal Antibody Therapy, 1988, vol. 45, p. 3.*
Neri et al, European Journal of Gynaecological Oncology, 1983, vol. 4, pp. 37–40. (abstract).*
Perlmann et al, Journal of Experimental Medicine, 1981, vol. 153, pp. 1592–1603.*
Deo et al, Journal of Immunology, Feb. 15, 1998 vol. 160, pp. 1677–1686. (abstract).*
Paul, Immunology (textbook), 1993, p. 934.*
Schlom, Molecular Foundations of Oncology (monograph), 1991, pp. 95–134.*
Castronovo V et al., "Possible role of human natural anti–Gal antibodies in the natural antitumor defense system," J Natl Cancer Inst. Feb. 1, 1989;81(3):212–6.
Clark JI et al., "Natural killer cell–directed bispecific antibodies", in *Bispecific Antibodies,* Fanger MW (ed.), RG Landis Co., Austin, pp. 77–88.
de Gast GC et al., "Clinical perspectives of bispecific antibodies in cancer," Cancer Immunol Immunother. Nov.–Dec. 1997;45(3–4):121–3.
Deo et al.,1998, J. of Immunol., 160: 1677 Abstract.
Desai PR et al., "Anti–Thomsen–Friedenreich (T) antibody–based ELISA and its application to human breast carcinoma detection," J Immunol Methods. Dec. 27, 1995;188(2):175–85.
Dodds and Sim (eds.), *Complement: A Practical Approach,* 1997, Oxford University Press.
Edberg JC et al., "Quantitative analyses of the relationship between C3 consumption, C3b capture, and immune adherence of complement–fixing antibody/DNA immune complexes," J Immunol. Dec. 15, 1988;141(12):4258–65.
Gorter A et al., "Expression of CD46, CD55, and CD59 on renal tumor cell lines and their role in preventing complement–mediated tumor cell lysis," Lab Invest. Jun. 1996;74(6):1039–49.
Gross DJ et al., "An immunochemical assay for natural IgM antibodies with an affinity to galactose and whose titer is reduced in the sera of cancer patients," Eur J Cancer Clin Oncol. Mar. 1988;24(3):363–7.
Hakomori S, "Tumor malignancy defined by aberrant glycosylation and sphingo(glyco)lipid metabolism," Cancer Res. Dec. 1, 1996;56(23):5309–18.

(List continued on next page.)

*Primary Examiner*—Anthony C. Caputa
*Assistant Examiner*—Karen A. Canella
(74) *Attorney, Agent, or Firm*—Pennie & Edmonds LLP

(57) ABSTRACT

The present invention relates to the treatment and prevention of cancer, viral infections and microbial infections by the administration of anti-C3b(i) antibodies. The present invention also relates to methods of treating and preventing cancer, viral infection, or microbial infection in an animal comprising administering to said animal IgG antibodies, IgM antibodies and/or complement components in combination with antibodies specific for C3b(i). The present invention also relates methods of treating and preventing cancer, viral infection or microbial infection in an animal comprising administrating said animal antibodies that immunospecifically bind to one or more cancer cell antigens, viral antigens or microbial antigens, respectively, in combination with antibodies immunospecific for C3b(i). The present invention further relates to the detection, imaging, diagnosis and monitoring of cancer utilizing C3b(i) specific antibodies.

46 Claims, 11 Drawing Sheets

OTHER PUBLICATIONS

Figure 1A:
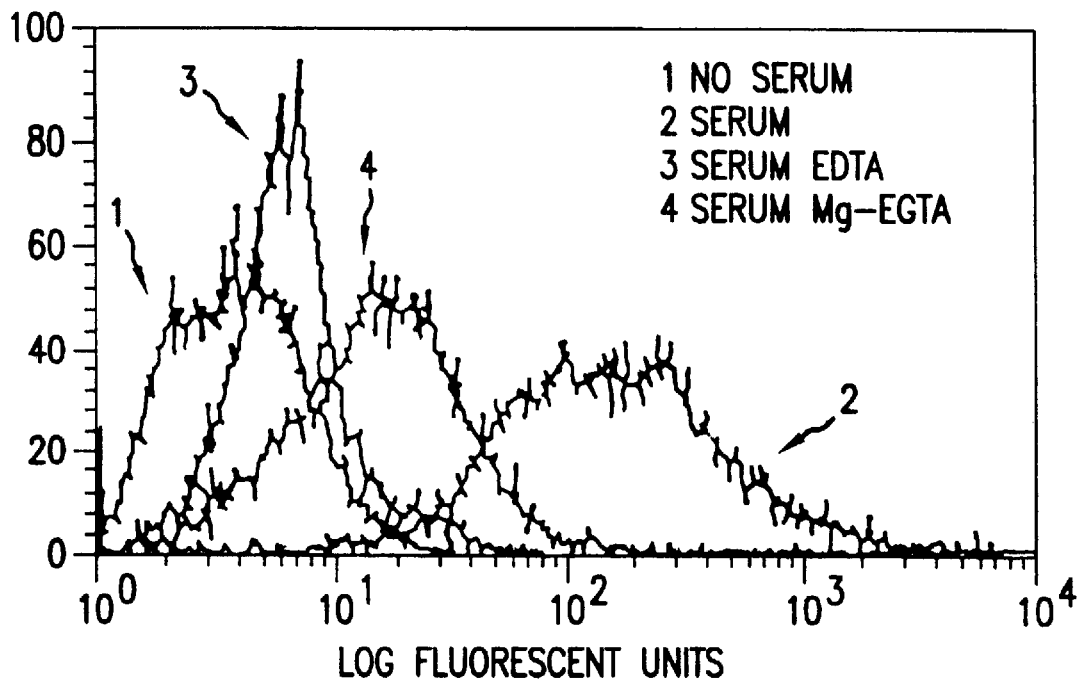

Higuchi et al., "Natural humoral immunity in patients with malignant diseases", J Clin Lab Immunol. 1980; 4:141–143.

Howard and Hughes Jones, 1988, Monoclonal Antibody Therapy, vol. 45, p. 3.

Irie et al., 1975, "Demonstration of In Vivo Reaction of Anti Body and Complement to Human Cancer Cells by Mixed Hemadsorption", Proc. Amer. Assoc. Cancer Res. vol. 16, p. 170, Abstract.

Irie K et al., "Evidence for in vivo reaction of antibody and complement to surface antigens of human cancer cells," Science. Nov. 1, 1974;186(4162):454–6.

Jarvis GA et al., Expression and function of the complement membrane attack complex inhibitor protectin (CD59) in human prostate cancer. Int J Cancer. Jun. 11, 1997;71(6):1049–55.

Maenpaa A et al., "Expression of complement membrane regulators membrane cofactor protein (CD46), decay accelerating factor (CD55), and protectin (CD59) in human malignant gliomas," Am J Pathol. Apr. 1996;148(4):1139–52.

Makrides SC et al., "Cell surface expression of the C3b/C4b receptor (CR1) protects Chinese hamster ovary cells from lysis by human complement," J Biol Chem. Dec. 5, 1992;267(34):24754–61.

Michael et al., "Synthesis of iC3b/C3d and Expression of a CD21–Like Protein by Malignant Epithelium", Growth Factors and Receptors I: Abstract 2167.

Mehta RL et al., "Binding and catabolism of aggregated immunoglobulins containing C3b by U937 cells," J Immunol. Mar. 1, 1986;136(5):1765–71.

Mollnes TE et al., "Activation of the third component of complement (C3) detected by a monoclonal anti–C3'g' neoantigen antibody in a one–step enzyme immunoassay," J Immunol Methods. Aug. 3, 1987;101(2):201–7.

Neri et al., 1983, J. of Gynaecological Oncology, 4:37 Abstract.

Niculescu F et al., "Persistent complement activation on tumor cells in breast cancer," Am J Pathol. May 1992;140(5):1039–43.

Okada H and Baba T, "Rosette formation of human erythrocytes on cultured cells of tumour origin and activation of complement by cell membrane," Nature. Apr. 5, 1974;248(448):521–2.

Paul et al., 1993, Immunology, p. 934.

Perlmann et al., 1982, "Interaction of Target Cell–Bound C3bi and C3d With Human Lymphocyte Receptors", J. Exp. Med. 153:1592–1603.

Petronis JD et al., "Indium–111 capromab pendetide (ProstaScint) imaging to detect recurrent and metastatic prostate cancer," Clin Nuc Med. Oct. 1998;23(10):672–7.

Reiter et al., 1989, "Killing of Human Tumor Cells by Antibody C3b Conjugates and Human Complement", Targeted Diagn Ther. 2:119–35.

Renner C et al., "Tumor therapy by immune recruitment with bispecific antibodies," Immunol Rev. Jun. 1995;145:179–209.

Schlom et al. 1991, "Monoclonal Antibodies: They're more or less than you think", Molecular Foundations of Oncology, pp. 95–134.

Seegal BC et al., "Immunoglobulins, complement and foreign antigens in human tumor cells," Int Arch Allergy Appl Immunol. 1976;52(1–4):205–11.

Segal DM et al., "T–cell targeted cytotoxicity" in *Bispecific Antibodies*, Fanger MW (ed.), RG Landis Co., Austin, pp. 27–42.

Springer GF, "Immunoreactive T and Tn epitopes in cancer diagnosis, prognosis, and immunotherapy," J Mol Med. Aug. 1997;75(8):594–602.

Springer GF, "T and Tn, general carcinoma autoantigens," Science. Jun. 15, 1984;224(4654):1198–206.

Tamerius et al., 1985, "Detection of a Neoantigen of Human C3bi and C3d by Monoclonal Antibody", J. of Immunology 135:2015.

Taylor RP et al., "Clearance of blood–borne pathogens mediated through bispecific monoclonal antibodies bound to the primate erythrocyte complement receptor," Cancer Immunol Immunother. Nov.–Dec. 1997;45(3–4):152–5.

Taylor RP et al., "Quantitative analyses of C3b capture and immune adherence of IgM antibody/dsDNA immune complexes," J Immunol. Dec. 1, 1989;143(11):3626–31.

Thornton BP et al., "Function of C3 in a humoral response: iC3b/C3dg bound to an immune complex generated with natural antibody and a primary antigen promotes antigen uptake and the expression of co–stimulatory molecules by all B cells, but only stimulates immunoglobulin synthesis by antigen–specific B cells," Clin Exp Immunol. Jun. 1996;104(3):531–7.

Taylor et al., 1991, "Use of heteropolymeric monoclonal antibodies to attach antigens to the C3b receptor of human erythrocytes: A potential therapeutic treatment", Proc. Natl. Acad. Sci. USA 88:3305–3309.

Tosic L et al., "Preparation of monoclonal antibodies to C3b by immunization with C3b(i)–sepharose," J Immunol Methods. Jun. 21, 1989;120(2):241–9.

Vetvicka V et al., Regulation of CR3 (CD11b/CD18)–dependent natural killer (NK) cell cytotoxicity by tumour target cell MHC class I molecules, Clin Exp Immunol. Feb. 1999;115(2):229–35.

Vetvicka V et al., "Targeting of natural killer cells to mammary carcinoma via naturally occurring tumor cell–bound iC3b and beta–glucan–primed CR3 (CD11b/CD18)," J Immunol. Jul. 15, 1997;159(2):599–605.

Vetvicka V et al., "Soluble beta–glucan polysaccharide binding to the lectin site of neutrophil or natural killer cell complement receptor type 3 (CD11b/CD18) generates a primed state of the receptor capable of mediating cytotoxicity of iC3b–opsonized target cells," J Clin Invest. Jul. 1, 1996;98(1):50–61.

Weisman HF et al., "Soluble human complement receptor type 1: in vivo inhibitor of complement suppressing post–ischemic myocardial inflammation and necrosis," Science. Jul. 13, 1990;249(4965):146–51.

Dempsey et al. C3d of complement as a molecular adjuvant: bridging innate and acquired immunity. Science. Jan. 19, 1996;271(5247):348–50.

Emery and Harris, Strategies for humanizing antibodies. In *Antibody Engineering* (2$^{nd}$ Ed.) Chapter 6, Borrebaeck ed. Oxford University Press, 1995 (pp 159–160 and 180–181 submitted herewith).

Seya et al. Complement–mediated tumor cell damage induced by antibodies against membrane cofactor protein (MCP, CD46). J Exp Med. Dec. 1, 1990;172(6):1673–80.

Tamerius et al. Detection of a neoantigen on human C3bi and C3d by monoclonal antibody. J Immunol. Sep. 1985;135(3):2015–9.

* cited by examiner

METHODS FOR THE PREVENTION AND TREATMENT OF CANCER USING ANTI-C3B (I) ANTIBODIES

This application is a continuation-in-part of U.S. application Ser. No. 09/392,500, filed Sep. 9, 1999, which is entitled to and claims priority benefits of application Ser. No. 60/099,782, filed Sep. 10, 1998 and application Ser. No. 60/123,786, filed Mar. 11, 1999, the entire disclosures of each of which are incorporated herein by reference.

This invention was made, in part, with government support under Grant Number AR43307 awarded by the National Institutes of Health. The United States government has certain rights in the invention.

1. INTRODUCTION

The present invention relates to methods of treating and preventing cancer, viral infection, or microbial infection in an animal comprising administrating to said animal antibodies specific for C3b(i). The present invention also relates to methods of treating and preventing cancer, viral infection, or microbial infection in an animal comprising administering to said animal IgG antibodies, IgM antibodies and/or complement components in combination with antibodies immunospecific for C3b(i). The present invention also relates methods of treating and preventing cancer, viral infection or microbial infection in an animal comprising administering to said animal antibodies that immunospecifically bind to one or more cancer cell antigens, viral antigens or microbial antigens, respectively, in combination with antibodies immunospecific for C3b(i). The present invention also relates to pharmaceutical compositions for the treatment and prevention of cancer, viral infection, and microbial infection comprising antibodies immunospecific for C3b(i). Further, the present invention relates to the detection, imaging, and diagnosis of cancer utilizing antibodies immunospecific for C3b(i).

2. BACKGROUND OF THE INVENTION

The complement system which is composed of some 21 plasma proteins plays an important role in the human immune system, both in the resistance to infections and in the pathogenesis of tissue injury. The activated products of the complement system attract phagocytic cells and greatly facilitate the uptake and destruction of foreign particles by opsonization. There are two distinct pathways for activating complement, the classical pathway and the alternate pathway, that result in conversion of C3 to C3b and subsequent responses (e.g., the formation of the membrane attack complex ("MAC")). Activation of the classical pathway is initiated by antigen-antibody complexes or by antibody bound to cellular or particulate antigens. The alternate pathway is activated independent of antibody by complex polysaccharides in pathogens such as bacterial wall constituents, bacterial lipopolysaccharides (LPS) and cell wall constituents of yeast (zymosan).

The classic complement pathway is initiated by the binding of C1 to immune complexes containing IgG or IgM antibodies. Activated C1 cleaves C2 and C4 into active components, C2a and C4b. The C4b2a complex is an active protease called C3 convertase, and acts to cleave C3 into C3a and C3b. C3b forms a complex with C4b2a to produce C4b2a3b, which cleaves C5 into C5a and C5b. C5b combines with C6, and the C5b6 complex combines with C7 to form the ternary complex C5b67. The C5b67 complex binds C8 to form the C5b678 complex which in turn binds C9 and results in the generation of the C5–C9 MAC. The insertion of the MAC into the cell membrane results the formation of a transmembrane channel that causes cell lysis.

In the alternative pathway, conversion of C3 to C3b (or C3i) produces a product that can combine with factor B, giving C3bB (or C3iB). These complexes are acted upon by factor D to generate C3bBb, which is a C3 convertase capable of cleaving more C3 to C3b, leading to more C3bBb and even more C3 conversion. Under certain circumstances the C3bBb complex is stabilized by association with the positive regulator properdin (P) by association of C3b and Bb. The C3 convertases can associate with an additional C3b subunit to form the C5 convertase, C3bBb C3b, which is active in the production of the C5–C9 MAC.

In both the classical and alternative pathways, the critical step in the activation of complement is the proteolytic conversion of C3 to the fragments C3b and C3a. C3a is an anaphylatoxin that attracts mast cells to the site of challenge, resulting in local release of histamine, vasodilation and other inflammatory effects. The nascent C3b has an ability to bind to surfaces around its site of generation and functions as a ligand for C3 receptors mediating, for example, phagocytosis.

Endogenous cell surfaces normally exposed to complement are protected by membrane-bound regulators such as decay accelerating factor ("DAF"), C59 ("protectin"), MCP, and the soluble C1 inhibitor or C1NH. DAF and MCP are responsible for limiting production of C3b and insure the generation of inactive forms of C3b, C3bi and C3dg from C3b. CD59 prevents attack of the MAC, which would otherwise destroy the cancer cell. C1 inhibitor binds to the active subcomponents of C1, C1r and C1s, and inhibits their activity.

2.1. Cancer Treatment

Despite advances in prevention and early detection, refinements in surgical technique, and improvements in adjuvant radiotherapy and chemotherapy, the ability to cure many patients of cancer remains elusive. This is especially pertinent to prostate cancer, which remains the most prevalent visceral tumor in American men, with approximately 180,000 new cases and nearly 40,000 deaths expected in 1999 (Landis et al., 1999, Cancer J Clin 49: 8–31). The continuing challenge of prostate cancer treatment is the successful management and eradication of recurrent, metastatic, and hormone-refractory disease, which accounts for the vast majority of prostate cancer-specific morbidity and mortality (Small, 1998, Drugs and Aging 13:71–81).

Many treatment modalities currently under investigation for prostate and other cancers depend upon tissue-specific delivery of anti-neoplastic agents. One immunotherapeutic approach involves conjugating cytotoxic agents to monoclonal antibodies (mAbs) specific for a particular cancer cell epitope. In this manner, the therapeutic agents can be delivered at a high therapeutic dose directly, and selectively, to the tumor site, thereby minimizing injury to healthy tissue (Bach et al., 1993, Immunol Today 14:421–5; Reithmuller et al., 1993, Cur. Op. Immunol 5:732–9; and Gruber et al., 1996, Spring Sem Immunopath 18:243–51). This method first requires the identification of specific epitopes for each cancer type. Such candidate epitopes must be expressed at high levels on the cancer cells compared to normal tissue. Second, this method requires the development of high affinity mAbs specific for these epitopes and these mAbs must show minimal cross-reactivity with self tissue. The biological mechanism of killing with mAbs will be variable, depending upon the epitopes identified on the cancer cells, and the effector functions of the specific mAb isotype. However, due to antigenic modulation and/or mutation, the cancer cells may reduce the available levels of the target epitope per cell, or eliminate it from their surface altogether. Thus, the use of mAbs in cancer diagnosis and treatment remains problematic.

A more widely applicable approach to treatment of cancer with mAbs would be to identify a ubiquitous antigenic site, present on virtually all cancer cells, and then to develop a panel of mAbs specific for this antigen. A voluminous literature reveals that cancer cells share certain common characteristics. Many types of human cancer cells are characterized by substantial abnormalities in the glycosylation patterns of their cell-surface proteins and lipids (Hakomori et. al., 1996, Canc Res. 56:5309–18; Castronovo et al., 1989, J Nat Canc Inst 81:212–6; Springer et al., 1984, Science 224:1198–206; and Springer et al., 1997, J Mol Med 75:594–602). These differences have led to the identification of antigenic determinants on cancer cells which are expressed at far lower levels on normal cells. Natural IgM antibodies to these epitopes are present in the circulation, and the interaction of such IgM antibodies with these cancer cell surface antigens leads to activation of complement and covalent coupling of complement activation products (C3b and its fragments, collectively referred to as C3b(i)) to the tumor cells (Okada et al., 1974, Nature 248:521–25; Irie et. al., 1974, Science 186:454–456; Desai et al., 1995, J Immunol Methods 188:175–85; Vetvicka et al., 1996, J Clin Invest 98:50–61; Vetvicka et al., 1997, J Immunol 159:599–605; and Vetvicka et al., 1999, Clin Exp Immunol 115:229–35). Although relatively large amounts of C3b(i) can be deposited on cancer cells, the concomitant expression of high levels of membrane-associated complement control proteins (e.g., decay accelerating factor ("DAF"), membrane cofactor protein ("MCP"), and, in particular, "protectin" i.e., CD59) usually prevents complement-mediated lysis (Cheung et al., 1988, J Clin Invest 81:1122–8; Gorter et al., 1996, Lab Invest 74:1039–49; Maenpaa et al., 1996, Am J Path 148:1139–52; and Li et al., 1997, Int J Canc 71:1049–55). Further, several investigators have established that in most cases, cancer patients have substantially lowered levels of the potentially protective IgM antibodies. Thus, in many cases the cancer cells cannot easily be killed by complement activation because of the reduced levels of protective IgM antibody and the increased expression of human complement control proteins on their surface.

2.2. Role of Complement in Infections

Innate immunity allows humans and most animals to respond to foreign organisms even before the initiation of the immune response. One of the most important aspects of innate immunity involves the complement system (Cooper, N. R. Complement and viruses. Volanakis, J. B. and Frank, M. M. The Human Complement System in Health and Disease. 18, 393–408. (1998) New York, Marcel Dekker, Inc.; and Petry, F. and Loos, M. Bacteria and complement. Volanakis, I. E. and Frank, M. M. The Human Complement System in Health and Disease. 171, 375–392. (1998) New York, Marcel Dekker, Inc.). It is now well-documented that a wide variety of bacteria, viruses and other microorganisms activate complement in the immunologically naive individual (Peterson et al., 1978, Infect. Immun. 19:943; Verbrugh et al., 1982, J. Immunol. 129:1681; Newman et al., 1985, J. Exp. Med. 161:1414; Seelen et al., 1995, Immunol. 84:653; Wagner et al., 1998, J. Immunol. 160:1936; Bakker et al., 1992, AIDS 6:35; Hiavacek et al., 1999, Proc. Nat!. Acad. Sci. 96:14681; Schmitz et al., 1994, J. Immunol. 153:1352; Tacnet-Delorme et al., 1999, J. Immunol. 162:4088; Joling et al., 1993, J. Immunol. 150:1065; Dominguez et al., 1999, J. Exp. Med. 189:25; and Washburn et al., 1991, Molec. Immunol. 28:465). These include, but are not limited to, both gram positive and gram negative bacteria, and the virus which causes AIDS, HIV. As a consequence of complement activation, these organisms are covalently labeled with complement activation fragments, and in particular with C3b(i). Moreover, in individuals with previous exposure to these pathogens (either through immunization or previous infection), specific antibodies will bind to the pathogens and also activate complement and promote C3b(i) deposition. Although in many instances this complement activation ultimately leads to the clearance and destruction of the microorganism, in some cases the C3b(i)-labeled invader remains in the circulation and can still infect susceptible tissues and organs. In fact, there are many examples of microorganisms which actually use these covalently attached C3b(i) molecules to gain entry into cells (which have receptors for C3bCi)) and establish productive infections (Bakker et al., 1992, AIDS 6:35; Tacnet-Delorme et al., 1999, J. Immunol. 162:4088; Cooper, N. R. Complement and viruses. Volanakis, J. B. and Frank, M. M. The Human Complement System in Health and Disease. 18, 393–408. 1998. New York, Marcel Dekker, Inc.; and Petry, F. and Loos, M. Bacteria and complement. Volanakis, I. E. and Frank, M. M. The Human Complement System in Health and Disease. 171, 375–392. (1998) New York, Marcel Dekker, Inc.). Several lines of evidence indicate that C3b(i)-opsonized HIV can persist in the body bound to the surface of dendritic cells for very long periods of time, and this cell-bound HIV may represent one of the main obstacles to the permanent elimination of HIV from the body (Hiavacek et al., 1999, Proc. Nat!. Acad. Sci. 96:14681; and Schmitz, et al., 1994,. J. Immunol. 153:1352).

Citation of a reference in this section or any section of this application shall not be construed as an admission that such reference is prior art to the present invention.

3. SUMMARY OF THE INVENTION

The present invention encompasses compositions comprising antibodies immunospecific for C3b(i) and methods for the treatment and prevention of cancer, viral infection, and microbial infection in an animal comprising administering such compositions to said animal. In particular, the present invention provides methods for treating or preventing cancer, viral infection, and microbial infection in animal comprising administering to said animal a therapeutically or prophylactically effective amount of an antibody immunospecific for C3b(i), an antibody immunospecific for C3b(i) covalently linked to a second molecule (e.g., an IgM antibody and IgG antibody, a glycoprotein or a glycolipid), a nucleic acid sequence encoding an antibody immunospecific for C3b(i), or a nucleic acid sequence encoding an antibody immunospecific for C3b(i) covalently linked to a second molecule. The present invention also provides methods for the treatment and prevention of cancer, viral infection, and microbial infection in an animal comprising administering to said animal IgG antibodies, IgM antibodies and/or complement components in combination with anti-C3b(i) antibodies. The present invention also provides methods for the treatment and prevention of cancer, viral infection, and microbial infection in an animal comprising administering to said animal antibodies immunospecific for one or more cancer cell antigens, viral antigens, or microbial antigens, respectively, in combination with anti-C3b(i) antibodies.

The present invention further provides methods for depleting cancer cells from cells obtained from an animal with cancer comprising contacting in vitro a sample comprising cells obtained from said animal with one or more antibodies immunospecific for C3b(i) or C3b(i) covalently linked to a second molecule.

The present invention also provides pharmaceutical compositions comprising one or more antibodies immunospecific for C3b(i) or C3b(i) covalently linked to a second molecule, in an amount effective for the treatment or prevention of cancer, a viral infection, or a microbial infection in an animal. The present invention also provides pharmaceutical compositions comprising one or more nucleic acid molecules encoding one or more antibodies immunospecific for C3b(i) or C3b(i) covalently linked to a second molecule, in an amount effective for the treatment or prevention of cancer, viral infection, or microbial infection in an animal. The present invention further provides a pharmaceutical composition comprising a bispecific antibody which is immunospecific for C3b(i) or C3b(i) covalently linked to a second molecule and an effector cell receptor or antigen, in an amount effective for the treatment or prevention of cancer, viral infection, or microbial infection in an animal.

The present invention encompasses methods for the detection, imaging, and diagnosis of cancer utilizing antibodies or fragments thereof immunospecific for C3b(i). The present invention provides methods for detecting cancer in an animal comprising: a) administering to said animal an effective amount of a labeled antibody that immunospecifically binds to C3b(i) or C3b(i) covalently linked to a second molecule; b) waiting for a time interval following the administering to permit the labeled antibody to preferentially concentrate at any cancerous site in the subject; c) determining background level; and d) detecting the labeled antibody in the animal, wherein detection of the labeled antibody above the background level indicates the presence of a cancer. The present invention also provides a method for detecting cancer in an animal, comprising imaging said subject at a time interval after administrating to said animal of an effective amount of a labeled antibody that immunospecifically binds to C3b(i) or C3b(i) covalently linked to a second molecule, said time interval being sufficient to permit the labeled antibody to preferentially concentrate at any cancerous site in said subject, wherein detection of the labeled antibody localized at said site in the animal indicates the presence of cancer.

The present invention provides kits comprising, in one or more containers, an antibody immunospecific for C3b(i) or C3b(i) covalently linked to a second molecule with instructions for use in the detection, imaging or diagnosis of cancer.

3.1. Definitions

The term "C3b(i)" as used herein refers to C3b and its fragments, including, but not limited to, C3b(i), C3b, and C3d.

As used herein, reference to an antibody immunospecific for C3b(i), C3b(i) specific antibodies, or anti-C3b(i) antibodies and the like shall be construed as including one or more antibodies immunospecific for C3b(i) covalently linked to a second molecule, unless indicated otherwise explicitly or by context. In a preferred embodiment, an anti-C3b(i) antibodies preferentially bind to C3b-opsonized cancer cells, and not C3b(i) in the mileau. In another preferred embodiment, anti-C3b(i) antibodies preferably bind to C3b(i) deposited on viruses or microbes, and not C3b(i) in the mileau.

The term "fusion protein" as used herein refers to a polypeptide that comprises an amino acid sequence of an antibody or fragment thereof and an amino acid sequence of a heterologous polypeptide (i.e., an unrelated polypeptide).

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

An "isolated" or "purified" antibody or fragment thereof, or polypeptide is substantially free of cellular material or other contaminating proteins from the cell or tissue source from which the protein is derived, or substantially free of chemical precursors or other chemicals when chemically synthesized. The language "substantially free of cellular material" includes preparations of an antibody, an antibody fragment, or a polypeptide in which the antibody, antibody fragment or polypeptide is separated from cellular components of the cells from which it is isolated or recombinantly produced. Thus, an antibody, an antibody fragment or a polypeptide that is substantially free of cellular material includes preparations of antibody, antibody fragment or polypeptide having less than about 30%, 20%, 10%, or 5% (by dry weight) of heterologous protein (also referred to herein as a "contaminating protein"). When the antibody, antibody fragment, or polypeptide is recombinantly produced, it is also preferably substantially free of culture medium, i.e., culture medium represents less than about 20%, 10%, or 5% of the volume of the protein preparation. When the antibody, antibody fragment or polypeptide is produced by chemical synthesis, it is preferably substantially free of chemical precursors or other chemicals, i.e., it is separated from chemical precursors or other chemicals which are involved in the synthesis of the protein. Accordingly such preparations of the antibody, antibody fragment, or polypeptide have less than about 30%, 20%, 10%, 5% (by dry weight) of chemical precursors or compounds other than the antibody, or polypeptide fragment of interest. In a preferred embodiment, antibodies of the invention or fragments thereof are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment, nucleic acid molecules encoding antibodies of the invention or fragments thereof are isolated or purified.

4. BRIEF DESCRIPTION OF THE FIGURES

FIG. 1 (A–D). Representative flow cytometry data from a study with serum from a normal donor (A, B) and a cancer patient (C, D). Measurement of C3b(i) (A, C) and IgM (B, D) deposition on C4-2 human prostate cancer cells is shown. Abundant C3b(i) is deposited on C4-2 cancer cells in response to the addition of normal human serum; this opsonization appears to be facilitated by both the classical and alternative complement pathways. After opsonization with serum from a prostate cancer patient, significantly less C3b(i) and IgM are deposited on the tumor cells (C, D). C3b(i) deposition via the alternative pathway (serum with Mg-EGTA), however, is comparable for both the normal and cancer patient serum, suggesting that the alternative pathway of the complement system remains intact in prostate cancer patient serum.

Figure 2A:
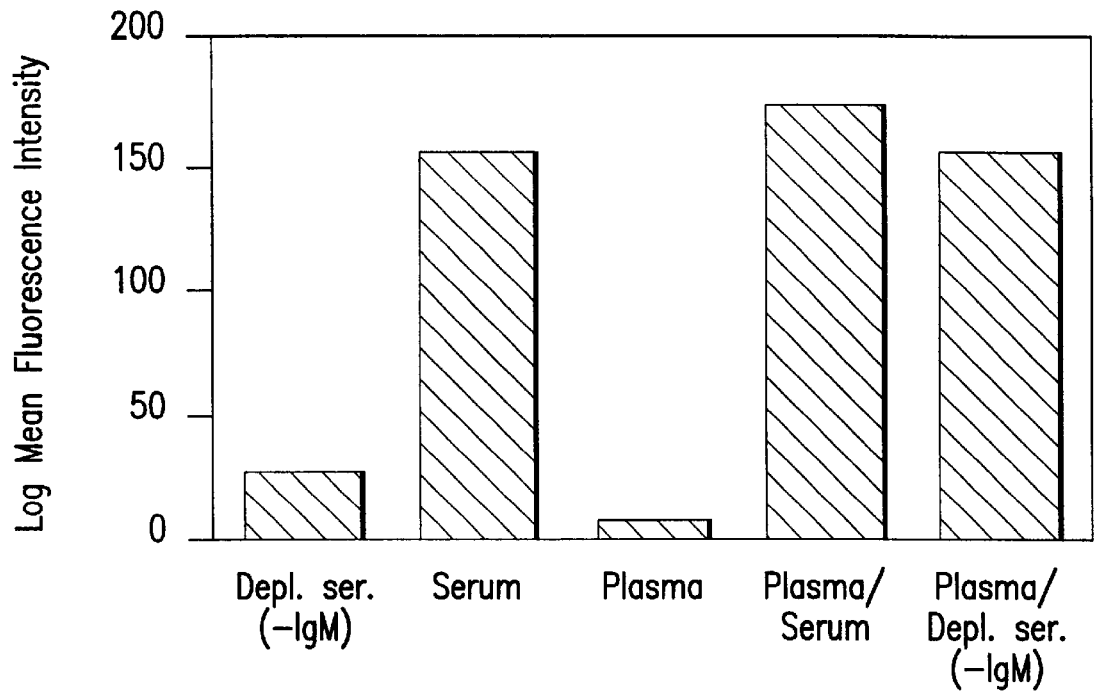

FIG. 2 (A–B). Flow cytometry (A) and radioimmunoassay (B) data demonstrating that removal of IgM from AB-positive serum results in a large reduction in the amount of C3b(i) that is deposited on LNCaP (A) or C4-2 (B) cells. C3b(i) deposition can be erstored with either whole normal human plasma (A, B) (e.g., plasma/IgM-depleted serum), whcih provides a source of human IgM, or with purified IgM/IgM-depleted serum (B).

Figure 3A:
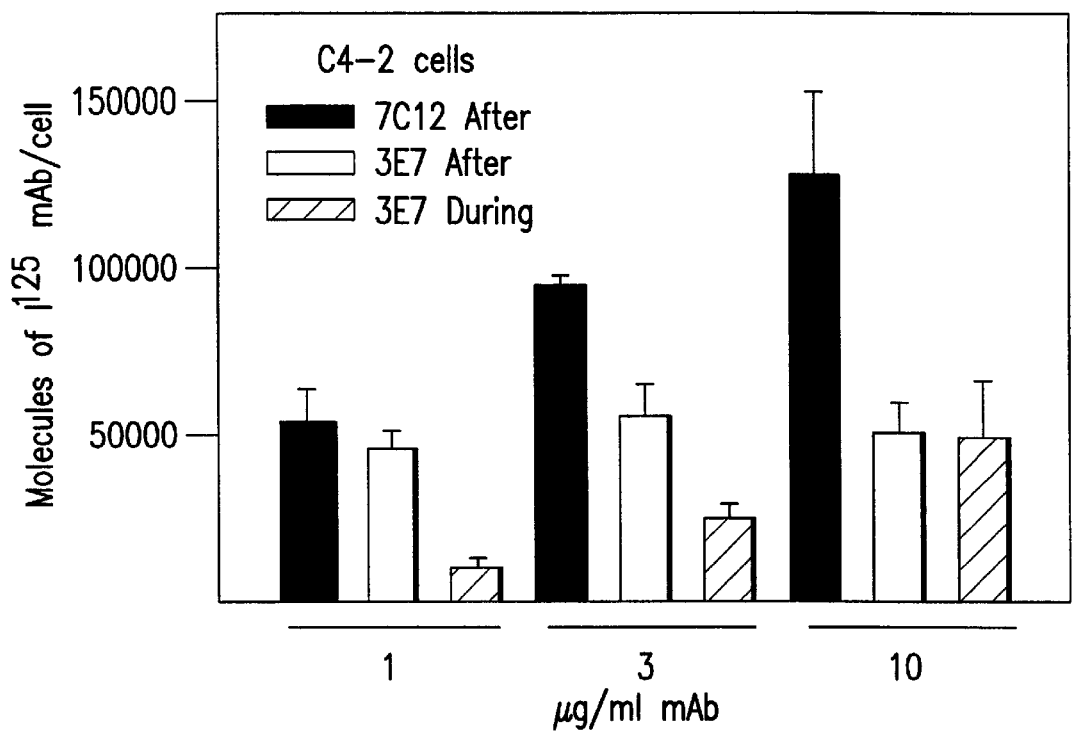
Figure 3B:
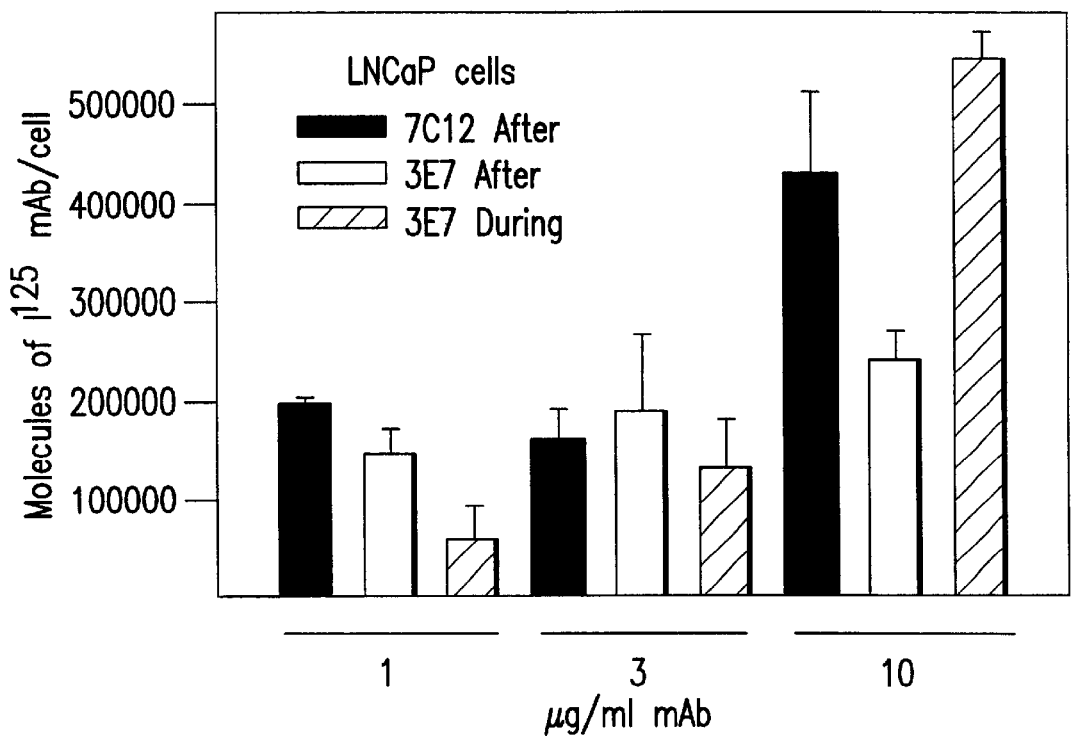

FIG. 3 (A–B). Radioimmunoassay data demonstrating that complement activation generates between 50,000 and 500,000 C3b(i) epitopes/opsonized cancer cell (net binding, background subtracted), as defined by binding of both $^{125}$I-labeled mAb 7C12 and 3E7. In panel A, an AB-positive serum was used for opsonization and, after three washes, cells were probed with differing amounts of the two mAb. Alternatively, mAb 3E7 was added to the cells just before the serum, and was present during opsonization. In panel B, AB-positive serum was used in conjunction with the 1-μg/ml and 10-μg/ml probes, and an AB-positive citrated plasma (different donor from that in A) was used for the 3-μg/ml probes FIG. 4. Flow cytometry results from surveys of sera from normal donors and patients with prostate cancer. Binding of human immunoglobulin to LNCaP and C4-2 prostate cancer cells was measured. Significant differences were determined by t-tests.

FIG. 5 (A–B). Immunohistochemical staining of normal (A) and neoplastic (B) human prostate tissue after incubation with anti-C3b(i) mAb.

Figure 6:
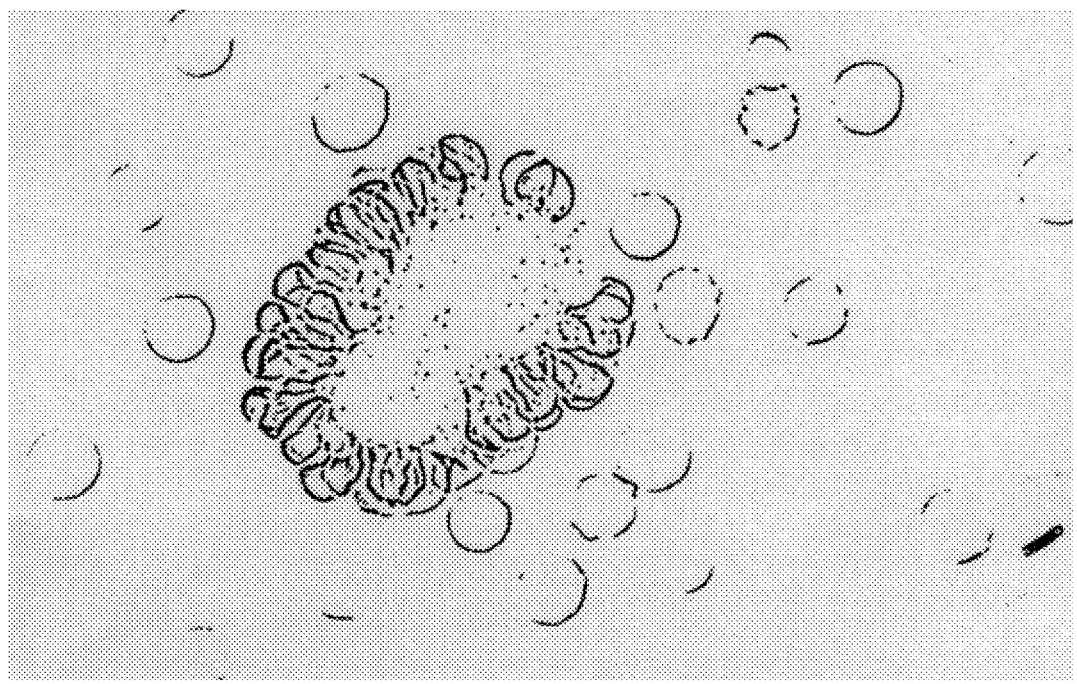

FIG. 6. Rosetting experiment using erythrocytes and opsonized LNCaP prostate cancer cells incubated in plasma in the presence of an anti-CR1 X anti-C3b(i) bispecific monoclonal antibody complex (7G9 X 3E7).

Figure 7A:
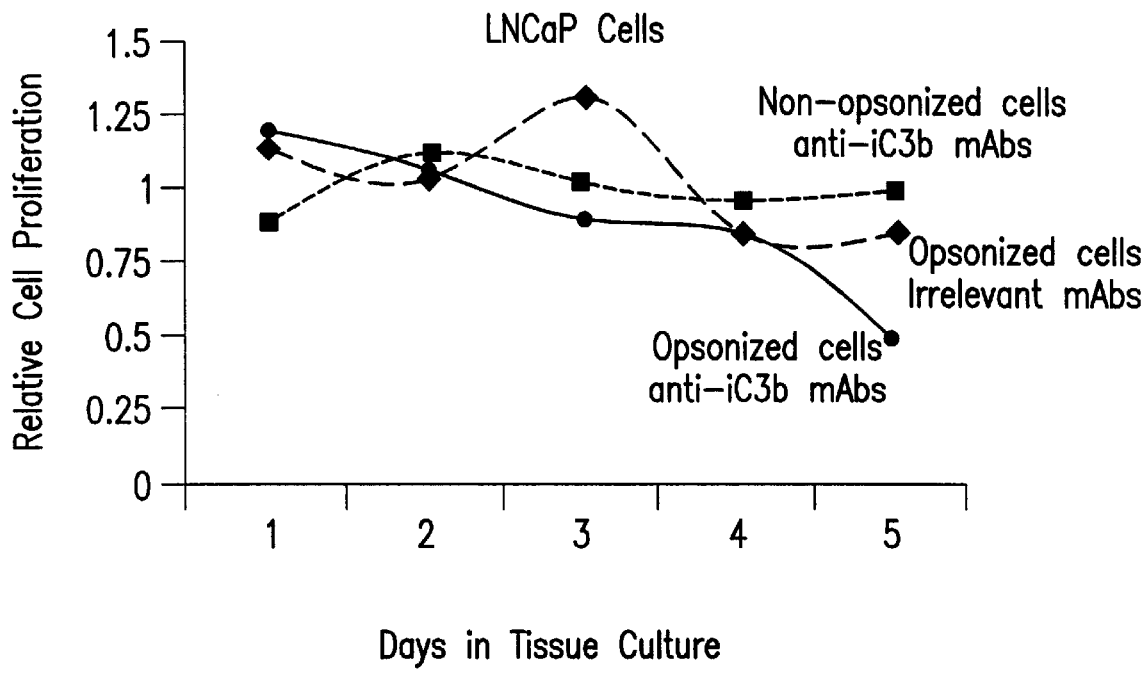
Figure 7B:
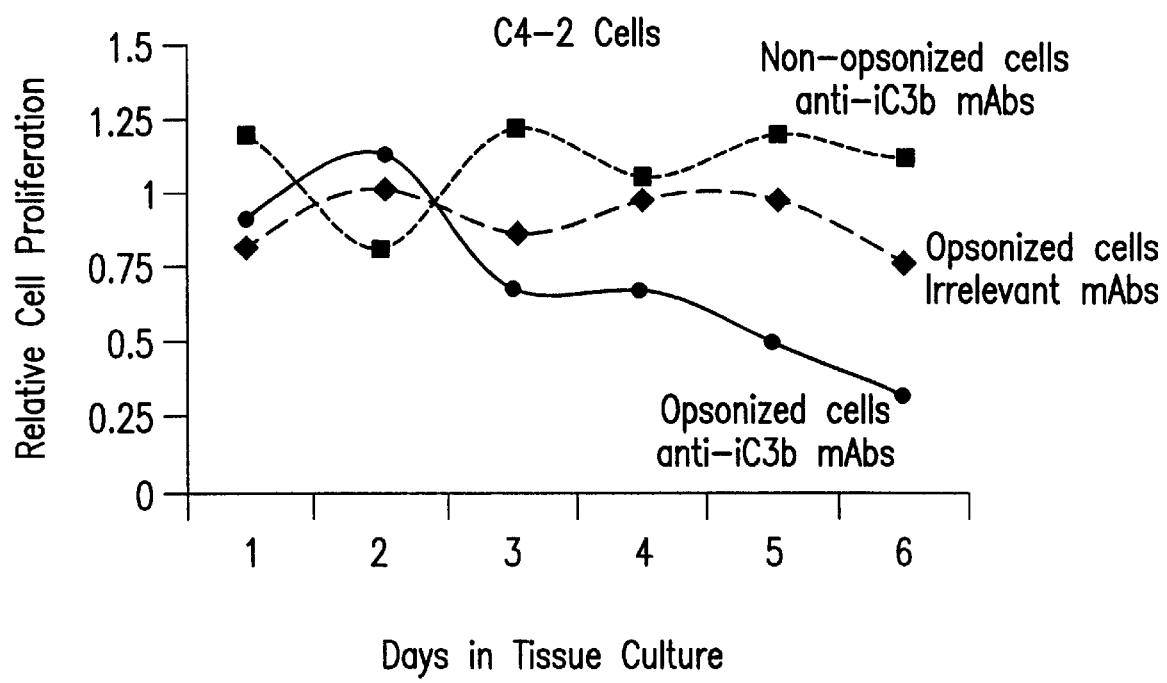

FIG. 7 (A–B). In vitro killing of LNCaP (A) and C4-2 (B) prostate cancer cells using $^{131}$I-labeled mAbs. Dashed line ( - - - ) delineates normal serum opsonized cells treated with $^{131}$I-labeled irrelevant mAbs; dotted line ( . . . ) delineates non-opsonized cells treated with $^{131}$I-anti-Cb3(i) mabs; solid line (—) delineates normal serum opsonized cells treated with $^{131}$I-labeled anti-C3b(i) mAbs. Measured as cell proliferation relative to non-treated cells.

Figure 8:
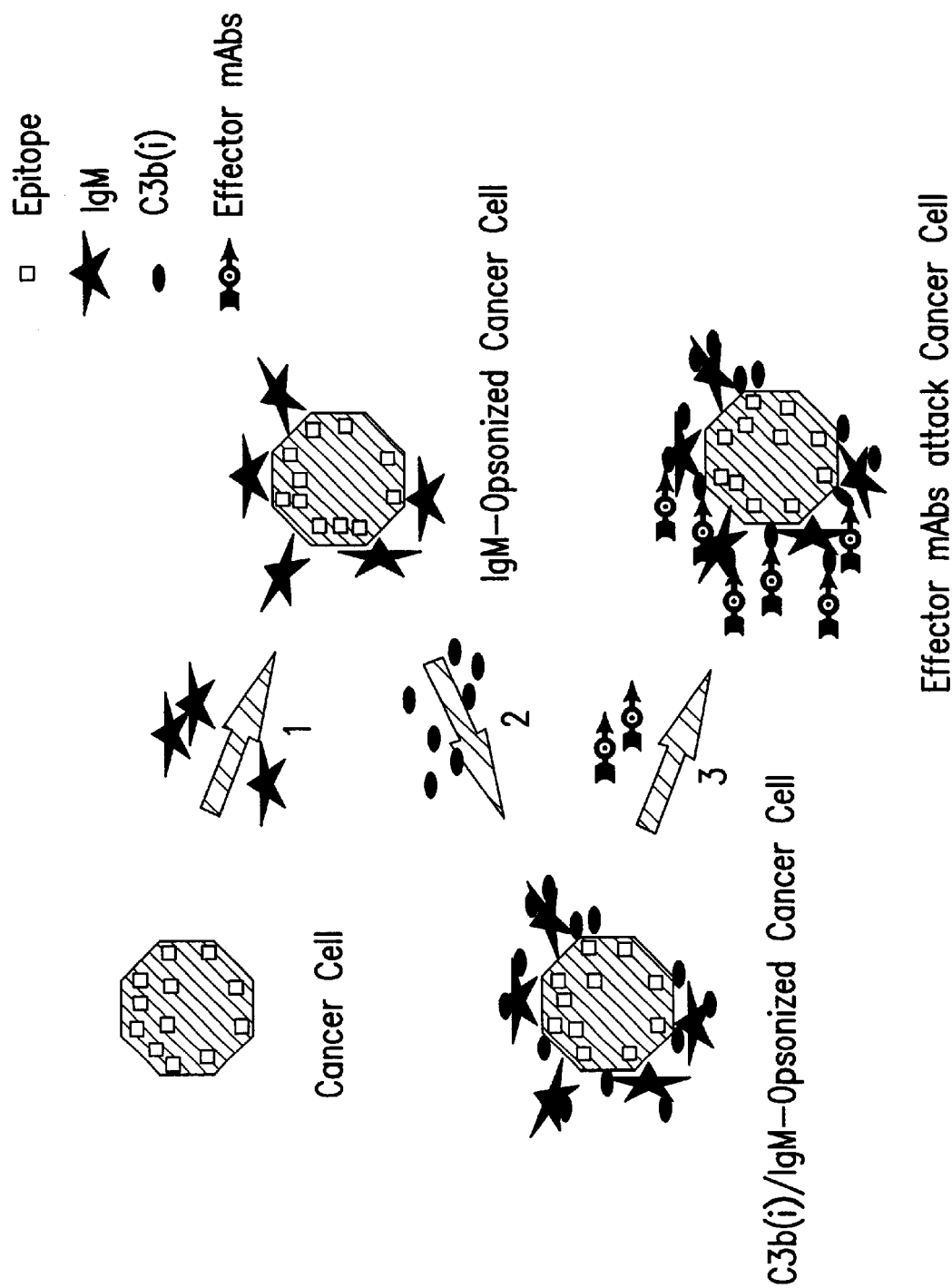

FIG. 8. The schematic illustrates the steps of the invention, all of which occur on the cell surface of tumor cells within the body of the cancer patient. In the first step, human IgM (either endogenous, or infused into the patient) binds to specific sites on the cancer cell. In the second step, complement (either endogenous, or infused into the patient as fresh plasma) is activated, and the resulting proteolytic fragment C3b(i) is deposited on the surface of the cancer cell. In the third step, a mAb specific for the C3b(i) epitope is administered. The mAb can be associated with a toxic, enzymatic, genetic, differentiating, and/or imaging agent (therefore it is an "effector mAb"), which results in the destruction or imaging of the cancer cell.

Figure 9:
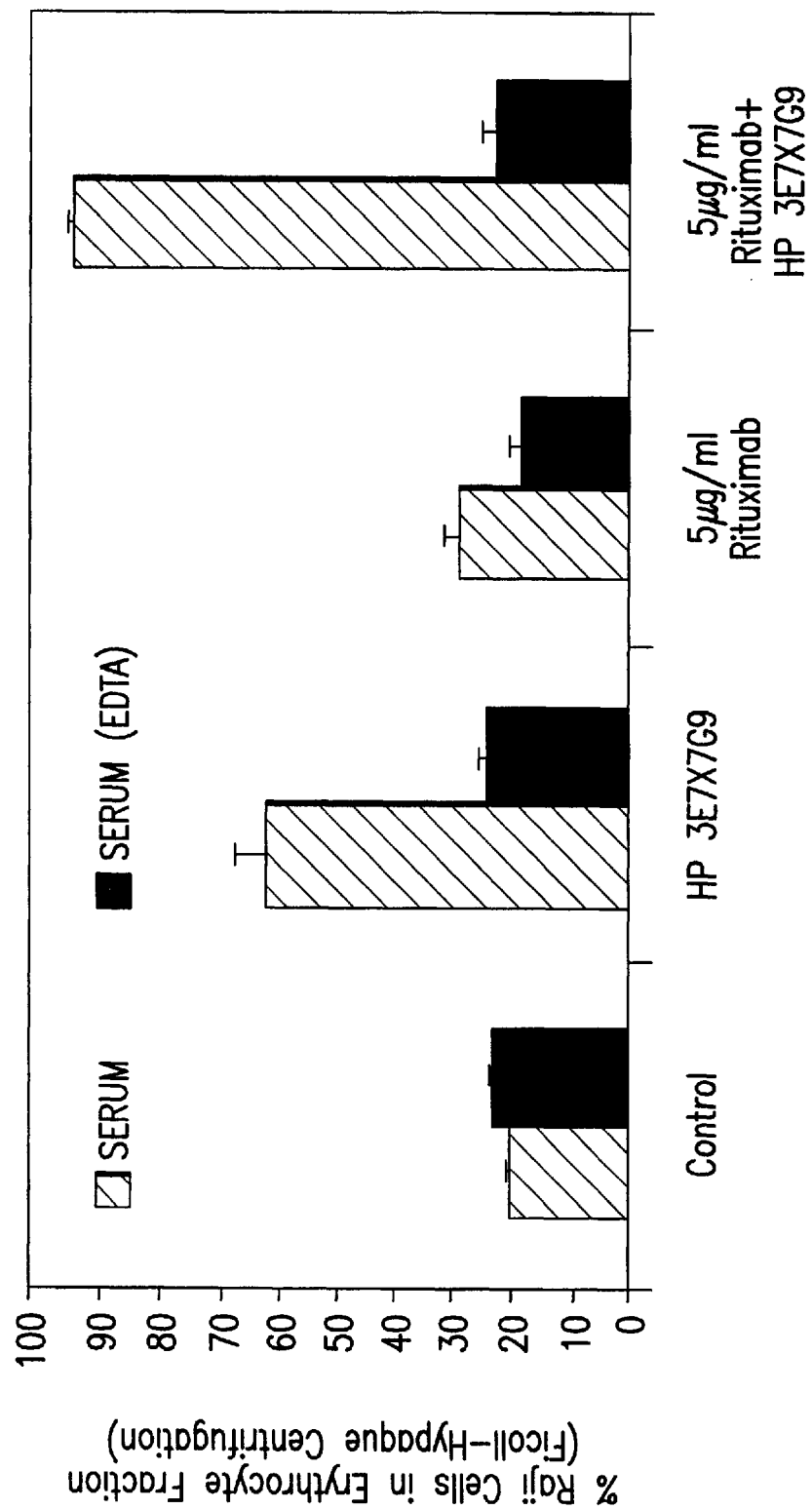

FIG. 9. Red cell binding experiment using erythrocytes and opsonized Rajii cells. Rajii cells treated with: serum alone; EDTA treated serum alone; serum and Rituximab; EDTA treated serum and Rituximab; serum and anti-C3b(i) X anti-CR1 bispecific monoclonal antibody complexes; EDTA treated serum and anti-C3b(i) X anti-CR1 bispecific monoclonal antibody complexes; serum, Rituximab, and anti-C3b(i) X anti-CR1 bispecific monoclonal antibody complexes; and EDTA treated serum Rituximab, and anti-C3b(i) X anti-CR1 bispecific monoclonal antibody complexes.

Figure 10:
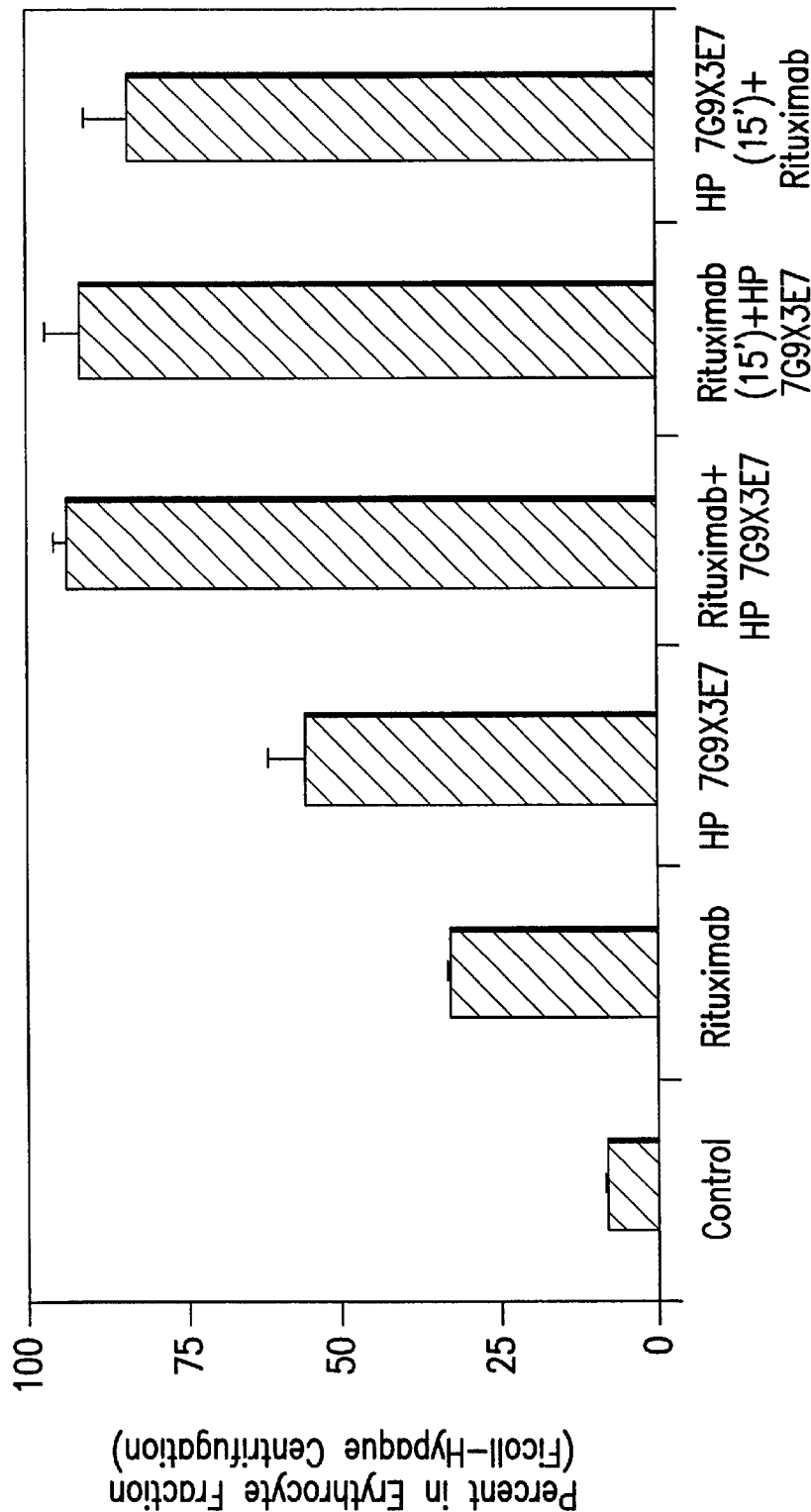

FIG. 10. Red cell binding experiment using erythrocytes and opsonized Rajii cells. Rajii cells treated with: washed whole blood reconstituted serum alone; washed whole blood reconstituted serum and Rituximab; washed whole blood reconstituted serum and anti-C3b(i) X anti-CR1 bispecific monoclonal antibody complexes; and washed whole blood reconstituted serum, Rituximab, and anti-C3b(i) X anti-CR1 bispecific monoclonal antibody complexes; washed whole blood reconstituted serum, Rituximab (15'), and anti-C3b(i) X anti-CR1 bispecific monoclonal antibody complexes; and washed whole blood reconstituted serum, anti-C3b(i) X anti-CR1 bispecific monoclonal antibody (15'), and Rituximab.

5. DETAILED DESCRIPTION OF THE INVENTION

The present invention encompasses compositions comprising one or more antibodies immunospecific for C3b(i) and the use of such compositions in the treatment and prevention of cancer, viral infection, and microbial infection. The present invention provides methods for treating or preventing cancer, viral infection, or microbial infection in an animal, said methods comprising administering to said animal a therapeutically or prophylactically effective amount of one or more antibodies immunospecific for C3b(i) or C3b(i) covalently linked to a second molecule. The present invention provides methods for treating or preventing cancer, viral infection, or microbial infection in an animal, said methods comprising administering to said animal IgG antibodies, IgM antibodies, and/or one or more complement components in combination with a therapeutically or prophylactically effective amount of one or more antibodies immunospecific for C3b(i) or C3b(i) covalently linked to a second molecule. The present invention further provides methods for treating or preventing cancer, viral infection, or microbial infection in animal, said methods comprising administering to said animal one or more antibodies immunospecific for one or more cancer antigens, viral antigens, or microbial antigens, respectively, in combination with one or more antibodies immunospecific for C3b(i) or C3b(i) covalently linked to a second molecule.

In accordance with the present invention, antibodies immunospecific for C3b(i) are administered to an animal, preferably a mammal and most preferably a human, to treat or prevent cancer, viral infection, or microbial infection. The antibodies of the present invention comprise monoclonal antibodies, polyclonal antibodies, bispecific antibodies, humanized antibodies, human antibodies, chimeric antibodies, single chain antibodies, Sfvs idiotypic antibodies, Fab fragments, and F(ab') fragments, fragments produced by a Fab expression library, and epitope-binding fragments. In a specific embodiment, monoclonal antibodies immunospecific for C3b(i) are administered to an animal, preferably a mammal and most preferably a human to treat or prevent cancer, viral infection, or microbial infection. In a preferred embodiment, monoclonal antibodies immuno-specific for C3b(i) covalently linked to a second molecule (e.g., an IgM antibody, an IgG antibody, a glycoprotein or glycolipid) are administered to an animal, preferably a mammal and most preferably a human, to treat or prevent cancer, viral infection, or microbial infection. In another embodiment, monoclonal antibodies immunospecific for C3b(i) are conjugated to a therapeutic moiety such as a chemotherapeutic cytotoxin, e.g., a cytostatic or cytocidal agent (e.g., paclitaxol, cytochalasin B or diphtheria toxin), a thrombotic or anti-angiogenic agent or a radioactive label. In another embodiment, monoclonal antibodies immunospecific for C3b(i) are conjugated to a detectable substrate such as, e.g., an enzyme, fluorescent marker, luminescent material, bioluminescent material, or radioactive material. In yet another embodiment, the valency of monoclonal antibodies immunospecific for C3b(i) are increased to that, for example, of a dimer or an IgM-like pentamer.

In a preferred embodiment, bispecific antibodies which are immunospecific for C3b(i) and an effector cell receptor or antigen are administered to an animal, preferably a mammal and most preferably a human, to treat, or prevent cancer, viral infection or microbial infection. The term "effector cell" as used herein refers to a cell which is involved in a cell-mediated immune response, said effector cells selected from the group, including, but not limited to, monocytes, macrophages, dendritic cells, neutrophils, natural killer cells, lymphocytes and erythrocytes. In one embodiment, anti-C3b(i) heteropolymer constructs (bispecific monoclonal complexes) bound ex vivo to an effector cell via a cell surface receptor are administered to an animal, preferably a mammal and most preferably a human; to treat or prevent cancer, viral infection or microbial infection. Cell surface receptors include, but are not limited to, CR1, CR2, CR3, CR4, human Fcγ receptors CD16, CD32 and CD64, and the Fc receptor for IgA, CD89. In a preferred embodiment, anti-C3b(i) heteropolymer constructs bound ex vivo to erythrocytes via CR1 are administered to an animal, preferably a mammal and most preferably a human, to treat, inhibit or prevent cancer.

In a preferred embodiment, bispecific diabodies which are antibody fragments immunospecific for C3b(i) and a complement component are administered to an animal, preferably a mammal and most preferably a human, to treat, inhibit or prevent cancer, viral infection, or microbial infection. In accordance with this embodiment, the diabodies are capable of recruiting complement components. In a preferred embodiment, bispecific diabodies which are immunospecific for C3b(i) and C1q are administered to an animal, preferably a mammal and most preferably a human, to treat or prevent cancer. Methods of preparing diabodies are taught in U.S. Pat. No. 5,837,242, which is incorporated herein in its entirety.

The present invention encompasses the administration of IgG antibodies and/or IgM antibodies in combination with one or more anti-C3b(i) antibodies to animals to facilitate the opsonization of cancer cells, viruses, and microbes. In one embodiment, IgG antibodies and/or IgM antibodies are administered to an animal prior to, subsequent to, or concomitantly with the administration of one or more antibodies immunospecific for C3b(i) to treat or prevent cancer, viral infection or microbial infection. In a preferred embodiment, IgG antibodies and/or IgM antibodies are administered to an animal prior to the administration of one or more antibodies immunospecific for C3b(i) to treat or prevent cancer, viral infection or microbial infection. In a specific embodiment, one or more antibodies immunospecific for one or more cancer cell antigens are administered to an animal prior to, subsequent to, or concomitantly with the administration of one or more antibodies immunospecific for C3b(i), in an amount effective for the treatment or prevention cancer. In a preferred embodiment, one or more antibodies immunospecific for one or more cancer cell antigens are administered to an animal prior to the administration of one or more antibodies immunospecific for C3b(i), in an amount effective for the treatment or prevention cancer. Examples of cancer cell antigens include, but are not limited to, improperly glycosylated cell-surface proteins and lipids.

In a specific embodiment, one or more antibodies used in cancer immunotherapy are administered to an animal prior to, subsequent to, or concomitantly with the administration of one or more anti-C3b(i) antibodies, in an amount effective for the treatment or prevention cancer. In a preferred embodiment, one or more antibodies used in cancer immunotherapy are administered to an animal prior to the administration of one or more anti-C3b(i) antibodies, in an amount effective for the treatment or prevention cancer. Examples of antibodies used in cancer immunotherapy include, but are not limited to: Herceptin® (Trastuzumab; Genetech, CA) which is a humanized anti-HER2 monoclonal antibody for the treatment of patients with metastatic breast cancer; Retuxan® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine $IgG_{2a}$ antibody for the treatment of colorectal cancer; BEC2 (ImClone Systems Inc., NY) which is murine IgG antibody for the treatment of lung cancer; IMC-C225 (Imclone Systems Inc., NY) which is a chimeric IgG antibody for the treatment of head and neck cancer; Vitaxin (MedImmune, Inc., MD) which is a humanized antibody for the treatment of sarcoma; Campath I/H (Leukosite, MA) which is a humanized $IgG_1$ antibody for the treatment of chronic lymphocytic leukemia (CLL); Smart MI95 (Protein Design Labs, Inc., CA) which is a humanized IgG antibody for the treatment of acute myeloid leukemia (AML); LymphoCide (Immunomedics, Inc., NJ) which is a humanized IgG antibody for the treatment of non-Hodgkin's lymphoma; Smart I D10 (Protein Design Labs, Inc., CA) which is a humanized antibody for the treatment of non-Hodgkin's lymphoma; Oncolym (Techniclone, Inc., CA) which is a murine antibody for the treatment of non-Hodgkin's lymphoma; the monoclonal antibody 7E11 which immunospecifically binds to prostate-specific membrane antigen (PSMA; Lin et al., 1997, Cancer Res. 57:3629); and the anti-CD20 monoclonal antibody sold by Beckman Coulter, Inc., CA.

In a specific embodiment, one or more antibodies immunospecific for one or more viral or microbial antigens are administered to an animal prior to, subsequent to, or concomitantly with the administration of one or more antibodies immunospecific for C3b(i), in an amount effective for the treatment or prevention of viral or microbial infection. Examples of antibodies used for the treatment or prevention of viral or mocrobial infection include, but are not limited to: Synagis® (MedImmune, Inc., MD) which is a humanized anti-respiratory syncytial virus (RSV) monoclonal antibody for the treatment of patients with RSV infection; PRO542 (Progenics) which is a CD4 fusion antibody for the treatment of HIV infection; Ostavir (Protein Design Labs, Inc., CA) which is a human antibody for the treatment of hepatitis B virus; Protovir (Protein Design Labs, Inc., CA) which is a humanized $IgG_1$ antibody for the treatment of cytomegalovirus (CMV); WIN1 which immunospecifically binds to LPS (Novardis) and mouse monoclonal anti-Legionella Pneumonia LPS (Research Diagnostics, Inc. NJ).

The present invention encompasses the administration of plasma as a source of IgG and/or IgM antibodies and one or more anti-C3b(i) antibodies for the treatment or prevention of cancer, viral infection, and microbial infection. In a specific embodiment, plasma or selectively enriched IgG and/or IgM antibodies is administered to an animal, preferably a mammal and most preferably a human, prior to, subsequent to, or concomitantly with the administration of one or more anti-C3b(i) antibodies in an amount effective for the treatment or prevention of cancer, viral infection or microbial infection. The plasma or selectively enriched IgG and/or IgM antibodies may be obtained from normal animals or from animals with a particular type of cancer, a particular type viral infection, or a particular type of microbial infection.

Preferably, the plasma or selectively enriched IgG and/or IgM is obtained from an animal of the same species which receives the administration. The plasma may or may not be treated with EDTA, citrate or heparin to block the complement pathways. In a specific embodiment, normal plasma or selectively enriched IgG and/or IgM antibodies from an animal, which contains antibodies immunospecific for cancer cell antigens (e.g., improperly glycosylated proteins or lipids) are administered to an animal prior to the administration of antibodies immunospecific for C3b(i). In another specific embodiment, normal plasma or selectively enriched IgG and/or IgM antibodies from an animal, which contains antibody immunospecific for a viral antigen or a microbial antigen (e.g., anti-HIV gp120 antibodies or anti-LPS antibodies). are administered to an animal prior to the administration of anti-C3b(i) antibodies.

The present invention encompasses the administration of recombinant complement components or plasma as a source of complement components and one or more anti-C3b(i) antibodies for the treatment or prevention of cancer, viral infection, and microbial infection In a specific embodiment, one or more complement components or recombinant complement components are administered to an animal, preferably a mammal and most preferably a human, prior to, subsequent to, or concomitantly with the administration of antibodies immunospecific for C3b(i). In another embodiment, normal plasma as a source of complement components is administered to an animal prior to, subsequent to, or concomitantly with the administration of antibodies immunospecific for C3b(i).

In a specific embodiment, a source of IgG and/or IgM antibodies and complement components (e.g., normal plasma) is administered to an animal to insure efficient opsonization prior to the administration of antibodies specific for C3b(i). In accordance with the invention, the administration of C3b(i) immunospecific antibodies in combination with IgG antibodies, IgM antibodies and/or complement components will initiate a chain reaction which results in increased complement activity and ultimately the killing of cancerous cells.

In a preferred embodiment, the endogenous levels of IgG antibodies, IgM antibodies and/or complement components are analyzed to determine whether an animal, preferably a mammal and most preferably a human, requires the administration of IgG antibodies, IgM antibodies and/or complement components. Standard techniques known to those of skill in the art can be utilized to measure the endogenous levels of IgG antibodies, IgM antibodies and complement components in an animal's sera. For example, the level of IgM antibodies or IgG antibodies in sera can be determined by titration of the sera against comparable cancer cell lines. Further, the level of complement components and complement activity can be determined by, for example, in vitro tests for the ability to interact with complement proteins and the ability to lyse target cells opsonized with specific antibodies complement. A Practical Approach, Dodds and Sim, Oxford University Press 1997; Makrides et al., 1992, J Biol. Chem. 264:24754–2476; and Weisman, H. F., et al., 1990, Science, 244:146–151). The present invention also provides compositions comprising one or more anti-C3b(i) antibodies use in the treatment, prevention, detection or diagnosis of cancer, viruses, and microbes.

The present invention provides methods and kits for depleting cancerous cells in vitro utilizing C3b(i) specific antibodies. The invention also provides methods and kits for the detection, imaging, and diagnosis of cancer utilizing antibodies specific for C3b(i). Further, the invention provides pharmaceutical compositions comprising antibodies specific for C3b(i).

5.1 IgG and IgM Enrichment

In accordance with certain embodiments of the present invention, the levels of IgG antibodies, IgM antibodies, and complement components in the sera or plasma of an animal are measured prior to the administration of anti-C3b(i) antibodies. In one embodiment, animals determined to have low levels of IgG antibodies and/or IgM antibodies are administered normal plasma containing IgG antibodies and/or IgM antibodies (preferably, IgG antibodies or IgM antibodies that immunspecifically bind to one or more cancer cell epitopes (e.g., improperly glycosylated proteins or lipids expressed by cancer cells), viral epitopes, or microbial epitopes) prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of anti-C3b(i) antibodies for the treatment or prevention of cancer, viral infection, or microbial infection. In accordance with this embodiment, the plasma is obtained from an animal of the same species that receives the plasma. In another embodiment, animals determined to have low levels of IgM antibodies are administered plasma enriched for IgM antibodies prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of anti-C3b(i) antibodies for the treatment or prevention of cancer, viral infection, or microbial infection. In another embodiment, animals determined to have low levels of IgG antibodies are administered plasma enriched for IgG antibodies prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of anti-C3b(i) antibodies for the treatment or prevention of cancer, viral infection, or microbial infection. In accordance with these embodiments, IgM antibodies or IgG antibodies are selectively enriched utilizing standard techniques known to those of skill in the art. Such techniques include, but are not limited to, chromatography, centrifugation, and differential solubility. In a particular embodiment of the invention, native or recombinant IgG antibodies or IgM antibodies known to immunospecifically bind to cancer cells, viruses or microbes are administered to an animal prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of anti-C3b(i) antibodies for the treatment or prevention of cancer. IgG antibodies or IgM antibodies that immunospecifically bind to one or more cancer cell antigens (e.g., improperly glycosylated proteins or lipids expressed by cancer cells), viral antigens (e.g., glycoprotein F of RSV and gp120 of HIV), or microbial antigens (e.g., LPS) can be purchased from a company or purified utilizing standard protein purification techniques known to those of skill in the art. Examples of standard protein purification techniques include, but are not limited to, gel purification, chromatography (e.g., ion exchange, affinity, particularly by affinity for the specific antigen after Protein A, and sizing column chromatography), centrifugation, and differential solubility. Recombinant IgG antibodies and IgM antibodies can be produced utilizing standard techniques known to those of skill in the art.

In one embodiment, plasma as a source of IgG and IgM antibodies is administered to an animal the same day as the animal is administered antibodies immunospecific for C3b(i) or C3b(i) covalently linked to a second molecule for the treatment or prevention of cancer, viral infections or microbial infections. In another embodiment, plasma as a source of IgG and IgM antibodies is administered to an animal a few minutes or hours (e.g., 15 minutes, 30 minutes, 45 minutes, 1 hour, 2 hours, 4 hours, 6 hours, 8 hours, 12 hours) before the antibodies immunospecific for C3b(i) or C3b(i) covalently linked to a second molecule are administered to the animal for the treatment or prevention of cancer, viral infections or microbial infections.

In a preferred embodiment, IgG antibodies and/or IgM antibodies are administered to an animal the same day as the animal is administered antibodies immunospecific for C3b(i) or C3b(i) covalently linked to a second molecule for the treatment or prevention of cancer, viral infections or microbial infections. In another preferred embodiment, IgG antibodies and/or IgM antibodies are administered to an animal a few minutes or hours (e.g., 5 minutes, 30 minutes, 45 minutes, 1 hour, 2 hours, 4 hours, 6 hours, 8 hours or 12 hours) before administering antibodies immunospecific for C3b(i) or C3b(i) covalently linked to a second molecule for the treatment or prevention of cancer, viral infections or microbial infections.

5.2 Complement Components

In a preferred embodiment, animals determined to have low levels of complement, particularly C3, are infused with normal plasma prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of anti-C3b(i) antibodies for the treatment or prevention of cancer, viral infection, or microbial infection. In accordance with this embodiment, the plasma is obtained from an animal of the same species that receives the plasma. In another preferred embodiment, animals determined to have low levels of complement are administered native or recombinant complement proteins (e.g., C3) prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of anti-C3b(i) antibodies for the treatment or prevention of cancer, viral infection, or microbial infection. In a specific embodiment, one or more complement components are administered to an animal the same day as the animal is administered anti-C3b(i) antibodies for the treatment or prevention of cancer, viral infection, or microbial infection. In another embodiment, one or more complement components are administered to an animal a few hours (e.g., 1 hour, 2 hours, 4 hours, 6 hours, 8 hours or 12 hours) before administering antibodies anti-C3b(i) antibodies for the treatment or prevention of cancer, viral infection, or microbial infection.

Complement components, in particular complement component C3, can be purchased from a company or purified utilizing standard protein purification techniques known to those of skill in the art. Examples of such purification techniques include, but are not limited to, gel purification, chromatography (e.g., ion exchange, affinity, particularly by affinity for the specific antigen after Protein A, and sizing column chromatography), centrifugation, and differential solubility. Recombinant complement components (e.g., C3) can be produced utilizing standard techniques known to those of skill in the art. In accordance with the invention, the nucleic acid sequences encoding complement components can be obtained from available sequence databases, e.g., GenBank. Both cDNA and genomic sequences can be cloned and expressed. Further, in accordance with the invention, the native or recombinant complement components administered to an animal for the treatment or prevention of cancer, viral infection, or microbial infection retain the ability to function in the classical and/or alternative complement pathways.

The nucleotide sequence encoding complement components or a functionally active analogs or other derivatives thereof (e.g., C3) can be inserted into an appropriate expression vector, i.e., a vector which contains the necessary elements for the transcription and translation of the inserted protein-coding sequence. For example, the nucleotide sequence encoding human C3 as disclosed in Genbank Accession Numbers NM_000064 and K02765 can be inserted into an appropriate expression vector. In another example, the nucleotide sequence encoding human C1 subcomponents, human C2 or human C2 as disclosed in Genbank Accession Numbers NM_000063, NM_001734, J04080, and AF019413, respectively, can be inserted into an appropriate expression vector. The necessary transcriptional and translational signals can be supplied by the native complement component genes or its flanking regions. A variety of host-vector systems may be utilized to express the protein-coding sequence. These include, but are not limited to, mammalian cell systems infected with virus (e.g., vaccinia virus, adenovirus, etc.); insect cell systems infected with virus (e.g., baculovirus); and microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In specific embodiments, the human complement component genes or sequences encoding functionally active portions of the human complement components are expressed.

Any of the methods known to one of skill in the art for the insertion of DNA fragments into a vector may be used to construct expression vectors containing a chimeric gene consisting of appropriate transcriptional and translational control signals and the protein coding sequences. These methods may include in vitro recombinant DNA and synthetic techniques and in vivo recombinants (genetic recombination). The expression of a nucleic acid sequence encoding a complement component or fragments thereof may be regulated by a second nucleic acid sequence so that the complement component or fragments thereof are expressed in a host transformed with the recombinant DNA molecule. The expression of complement components (e.g., C3) may be controlled by any promoter or enhancer element known to one of skill in the art. In particular, the expression of a complement component may regulated by any constitutive promoter, inducible promoter, tissue specific promoter, or native complement component promoter known to one of skill in the art.

Promoters which may be used to regulate the expression of a complement component (e.g., C3) include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. USA 78:1441–1445), the regulatory sequences of the metallothionein gene (Brinster et al., 1982, Nature 296:39–42); prokaryotic expression vectors such as the β-lactamase promoter (Villa-Kamaroff et al., 1978, Proc. Natl. Acad. Sci. USA 75:3727–3731), or the tac promoter (DeBoer et al., 1983, Proc. Natl. Acad. Sci. USA 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, *Nature* 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58, alpha 1-antitrypsin gene control region which is active in the liver (Kelsey et al., 1987, Genes and Devel. 1:161–171), beta-globin gene control region which is active in myeloid cells (Mogram et al., 1985, Nature 315 :338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378). In certain embodiments, the promoter regulating the expression of the complement component is a constitutive promoter. In certain other embodiments, the promoter regulating the expression of the complement component is an inducible or tissue-specific promoter.

In a specific embodiment, the vector used to express a complement component comprises a promoter operably linked to a complement component (e.g., C3)-encoding nucleic acid, one or more origins of replication, and, optionally, one or more selectable markers (e.g., an antibiotic resistance gene).

Expression vectors containing nucleotide sequences encoding one or more complement components can be identified by three general approaches: (a) nucleic acid hybridization; (b) presence or absence of "marker" gene functions: and (c) expression of inserted sequences. In the first approach, the presence of a nucleotide sequence encoding a complement component (e.g., C3) in an expression vector(s) can be detected by nucleic acid hybridization using probes comprising sequences that are homologous to the inserted nucleotide sequence. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of the nucleotide sequence encoding the complement component in the vector(s). For example, if a nucleotide sequence encoding C3 is inserted within the marker gene sequence of the vector, recombinant vectors containing the nucleotide sequence can be identified by the absence of the marker gene function. In the third approach, recombinant expression vectors can be identified by assaying for RNA or polypeptides encoded by the nucleotide sequence for the complement component. Such assays can be based, for example, on the physical or functional properties of the complement component in in vitro assay systems, e.g., binding of C3 with anti-C3 antibody.

A host cell can be transfected with a nucleotide sequence encoding a complement component or a vector comprising a nucleotide sequence encoding a complement component using techniques known to those of skill in the art such as, for example, microinjection, electroporation, lipofection, and calcium phosphate precipitation. Host cells may be stably or transiently transfected with a nucleotide sequence encoding a complement component or a vector comprising a nucleotide sequence encoding a complement component.

For long-term, high-yield production of one or more recombinant complement components, stable expression is preferred. For example, cell lines which stably express one or more complement components may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Once a suitable host system and growth conditions are established, recombinant expression vectors can be propagated and prepared in quantity. A host cell strain can be chosen which modulates the expression of the inserted sequences in the specific fashion desired. Appropriate cell lines or host systems can be chosen to ensure the desired modification and processing of the complement protein expressed. Different host cells have characteristic and specific mechanisms for the translational and post-translational processing and modification (e.g., glycosylation and phosphorylation) of proteins. For example, expression in a bacterial system can be used to produce an unglycosylated core protein product. Expression in yeast will produce a glycosylated product. Expression in mammalian cells can be used to ensure "native" glycosylation of a heterologous protein. Such mammalian host cells include, but are not limited to, 293T, CHO, VERY, BHK, Hela, COS, MDCK, 293, 3T3, MT2, U937, WI38, BT483, Hs578T, HTB2, BT20, T47D, CRL7030, Hs578Bst, lymphocytes and fibroblasts. Furthermore, different vector/host expression systems may effect processing reactions to different extents.

5.3 Antibodies

Antibodies of the invention include, but are not limited to, polyclonal, monoclonal, bispecific, human, humanized or chimeric antibodies, single chain antibodies, sFvs fragments, F(ab') fragments, fragments produced by a Fab expression library, anti-idiotypic (anti-Id) antibodies, and epitope-binding fragments of any of the above which immunospecifically bind to cancer cell antigens, viral antigens, microbial antigens, C3b(i) or fragments thereof, or C3b(i) covalently linked to a second molecule. The term "antibody" as used herein refers to immunoglobulin molecules and immunologically active portions of immunoglobulin molecules, i.e., molecules that contain an antigen binding site which immunospecifically binds a cancer cell antigen, a viral antigen, a microbial antigen, C3b(i), or C3b(i) covalently linked to a second molecule. The immunoglobulin molecules of the invention can be of any type (e.g., IgG, IgE, IgM, IgD and IgA), class, or subclass of immunoglobulin molecule.

Polyclonal antibodies which may be used in the methods of the invention are heterogeneous populations of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies which may be used in the methods of the invention are homogeneous populations of antibodies to a particular antigen (e.g., a cancer cell antigen, a viral antigen, a microbial antigen, or C3b(i)). A monoclonal antibody (mAb) to an antigen-of-interest can be prepared by using any technique known in the art which provides for the production of antibody molecules by continuous cell lines in culture. These include but are not limited to, the hybridoma technique originally described by Kohler and Milstein (1975, Nature 256, 495–497), the more recent human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77–96). Such antibodies may be of any immunoglobulin class including IgG, IgM, IgE, IgA and, IgD and any subclass thereof. The hybridoma producing the mAbs of use in this invention may be cultivated in vitro or in vivo.

The monoclonal antibodies which may be used in the methods of the invention include, but are not limited to, human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80, 7308–7312; Kozbor et al., 1983, Immunology Today 4, 72–79; and Olsson et al., 1982, Meth. Enzymol. 92, 3–16).

The invention further provides for the use of bispecific antibodies. Methods for making bispecific antibodies are known in the art. Traditional production of full length bispecific antibodies is based on the coexpression of two immunoglobulin heavy chain-light chain pairs, where the two chains have different specificities (Milstein et al., 1983, Nature 305:537–539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low.

Similar procedures are disclosed in PCT Publication No. WO 93/08829, published May 13, 1993, and in Traunecker et al., 1991, EMBO J. 10:3655–3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT Publication No. WO 94/04690 published Mar. 3, 1994, which is incorporated herein by reference in its entirety.

For further details of generating bispecific antibodies see, for example, Suresh et al., Methods in Enzymology, 1986, 121:210. Using such techniques, a bispecific molecule which combines anti-C3b(i) antibody and an antibody specific for an effector cell receptor or antigen can be prepared for use in the treatment or inhibition of disease as defined herein.

The invention provides for the use of functionally active fragments, derivatives or analogs of antibodies which immunospecifically bind to cancer cell antigens, viral antigens, and microbial antigens. Functionally active means that the fragment, derivative or analog is able to elicit anti-anti-idiotype antibodies that recognize the same antigen that the antibody from which the fragment, derivative or analog is derived recognized. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay)

Other embodiments of the invention include fragments of the antibodies of the invention such as, but not limited to, F(ab')$_2$ fragments, which contain the variable region, the light chain constant region and the CH1 domain of the heavy chain can be produced by pepsin digestion of the antibody molecule, and Fab fragments, which can be generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g., as described in U.S. Pat. No. 4,946,778; Bird, 1988, Science 242:423–42; Huston et al., 1988, Proc. Natl. Acad. Sci. USA 85:5879–5883; and Ward et al., 1989, Nature 334:544–54), or any other molecule with the same specificity as the antibody of the invention.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine monoclonal and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041–1043; Liu et al., 1987, Proc. Natl. Acad. Sci. USA 84:3439–3443; Liu et al., 1987, J. Immunol. 139:3521–3526; Sun et al., 1987, Proc. Natl. Acad. Sci. USA 84:214–218; Nishimura et al., 1987, Canc. Res. 47:999–1005; Wood et al., 1985, Nature 314:446–449; and Shaw et al., 1988, J. Natl. Cancer Inst. 80:1553–1559; Morrison, 1985, Science 229:1202–1207; Oi et al., 1986, Bio/Techniques 4:214; U.S. Pat. No. 5,225,539; Jones et al., 1986, Nature 321:552–525; Verhoeyan et al. (1988) Science 239:1534; and Beidler et al., 1988, J. Immunol. 141:4053–4060; each of which is incorporated herein by reference n its entirety.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806; each of which is incorporated herein by reference in its entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Bio/technology 12:899–903).

In other embodiments, the invention provides fusion proteins of the antibodies of the invention (or functionally active fragments thereof), for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not the antibody. Preferably, the antibody or fragment thereof is covalently linked to the other protein at the N-terminus of the constant domain.

The antibodies of the invention include analogs and derivatives that are either modified, i.e, by the covalent attachment of any type of molecule as long as such covalent attachment does not prevent the antibody from generating an anti-idiotypic response. For example, but not by way of limitation, the derivatives and analogs of the antibodies include those that have been further modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the analog or derivative may contain one or more non-classical amino acids.

The antibodies of the invention include antibodies with modifications (e.g., substitutions, deletions or additions) in amino acid residues that interact with Fc receptors. In particular, the antibodies of the invention include antibodies with modifications in amino acid residues identified as involved in the interaction between the Fc domain and the FcRn receptor (see, e.g., PCT Publication No. WO 97/34631, which is incorporated herein by reference in its entirety).

5.3.1 Anti-C3b(i) Antibodies

In a specific embodiment, anti-C3b(i) antibodies are immunospecific for C3b(i) or a fragment thereof. In another embodiment, anti-C3b(i) antibodies are immunospecific for C3b(i) covalently linked to a second molecule. In a preferred embodiment, anti-C3b(i) antibodies are monoclonal antibodies. In another preferred embodiment, anti-C3b(i) antibodies are immunospecific for C3b(i) covalently bound to IgG or IgM antibodies and said anti-C3b(i) antibodies have minimal cross-reactivity with C3b(i) in the media. In another preferred embodiment, anti-C3b(i) antibodies are immunospecific for C3b(i) covalently bound to a cancer cell, or C3b(i) covalently bound to a virus or microbe; and said anti-C3b(i) antibodies have minimal cross-reactivity with C3b(i) in the media. In yet another preferred embodiment, anti-C3b(i) antibodies administered to humans are humanized or human monoclonal antibodies.

Anti-C3b(i) antibodies can be obtained from any organization (e.g., a university scientist or a company such as Research Diagnostics Inc. in New Jersey) or produced by any method known to one of skill in the art. For example, anti-C3b(i) antibodies can be produced by chemical synthesis or recombinant expression techniques. The nucleotide sequence encoding an anti-C3b(i) antibodies can be obtained, e.g., from the GenBank database or a database like it, the literature publications, or by routine cloning and sequencing.

5.3.2 Antibodies Immunospecific for Cancer Cells

In a specific embodiment, antibodies immunospecific for a cancer cell antigen for use in accordance with methods of the invention are monoclonal antibodies. Preferably, antibodies immunospecific for a cancer cell antigen which are administered to humans are humanized or human monoclonal antibodies. As used herein, the term "cancer cell antigen" refers to an antigen that is preferentially or differentially expressed on cancer cells relative to non-cancerous cells, preferably normal cells. Examples of cancer cell antigens include, but are not limited, to improperly glycosylated proteins and lipids, CD20, Her2, and PSMA.

Antibodies immunospecific for a cancer cell antigen can be obtained from any organization (e.g., a university scientist or a company such as Genentech) or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment or prevention cancer are used in accordance with the methods of the invention. Examples of antibodies available for the treatment of cancer include, but are not limited to, Herceptin® (Trastuzumab; Genetech, CA) which is a humanized anti-HER2 monoclonal antibody for the treatment of patients with metastatic breast cancer; Retuxan® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine $IgG_{2a}$ antibody for the treatment of colorectal cancer; BEC2 (ImClone Systems Inc., NY) which is murine IgG antibody for the treatment of lung cancer; IMC-C225 (Imclone Systems Inc., NY) which is a chimeric IgG antibody for the treatment of head and neck cancer; Vitaxin (MedImmune, Inc., MD) which is a humanized antibody for the treatment of sarcoma; Campath I/H (Leukosite, MA) which is a humanized $IgG_1$ antibody for the treatment of chronic lymphocytic leukemia (CLL); Smart M195 (Protein Design Labs, Inc., CA) which is a humanized IgG antibody for the treatment of acute myeloid leukemia (AML); LymphoCide (Immunomedics, Inc., NJ) which is a humanized IgG antibody for the treatment of non-Hodgkin's lymphoma; Smart I D10 (Protein Design Labs, Inc., CA) which is a humanized antibody for the treatment of non-Hodgkin's lymphoma; and Oncolym (Techniclone, Inc., CA) which is a murine antibody for the treatment of non-Hodgkin's lymphoma.

5.3.3 Antibodies to Viral and Microbial Antigens

In a specific embodiment, antibodies immunospecific for a viral or microbial antigen for use in accordance with methods of the invention are monoclonal antibodies. Preferably, antibodies immunospecific for a viral antigen or microbial antigen which are administered to humans are humanized or human monoclonal antibodies. As used herein, the term "viral antigen" refers to any viral polypeptide or protein (e.g., HIV gp120 and RSV F glycoprotein which is capable of eliciting an immune response. As used herein, the term "microbial antigen" refers to any microbial polypeptide, protein, or lipid molecule (e.g., a bacterial, fungi, pathogenic protozoa or yeast polypeptide including, e.g., LPS and capsular polysaccharide 5/8) which is capable of eliciting an immune response.

Antibodies immunospecific for a viral or microbial antigen can be obtained from any organization (e.g., a university scientist or a company such as Genentech) or produced by any method known to one of skill in the art such as, e.g., chemical synthesis or recombinant expression techniques. The nucleotide sequence encoding antibodies immunospecific for a viral or microbial antigen can be obtained, e.g., from the GenBank database or a database like it, the literature publications, or by routine cloning and sequencing.

In a specific embodiment, known antibodies for the treatment or prevention viral or microbial infection are used in accordance with the methods of the invention. Examples of antibodies available for the treatment of viral infection or microbial infection include, but are not limited to, Synagis(® (MedImmune, Inc., MD) which is a humanized anti-respiratory syncytial virus (RSV) monoclonal antibody for the treatment of patients with RSV infection; PRO542

(Progenics) which is a CD4 fusion antibody for the treatment of HIV infection; Ostavir (Protein Design Labs, Inc., CA) which is a human antibody for the treatment of hepatitis B virus; Protovir (Protein Design Labs, Inc., CA) which is a humanized IgG$_1$ antibody for the treatment of cytomegalovirus (CMV); and anti-LPS antibodies.

5.4 Production of Recombinant Antibodies

The antibodies of the invention can be produced by any method known in the art for the synthesis of antibodies, in particular, by chemical synthesis or by recombinant expression, and are preferably produced by recombinant expression techniques.

Recombinant expression of the antibodies of the invention, or fragment, derivative or analog thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody may be generated from a suitable source. If a clone containing the nucleic acid encoding the particular antibody is not available, but the sequence of the antibody is known, a nucleic acid encoding the antibody may be obtained from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

If an antibody that specifically recognizes a particular antigen is not available (or a source for a cDNA library for cloning a nucleic acid encoding such an immunoglobulin), antibodies specific for a particular antigen may be generated by any method known in the art, for example, by immunizing an animal, such as a rabbit, to generate polyclonal antibodies or, more preferably, by generating monoclonal antibodies, e.g., as described by Kohler and Milstein (1975, *Nature* 256:495–497) or, as described by Kozbor et al. (1983, *Immunology Today* 4:72) or Cole et al. (1985 in *Monoclonal Antibodies and Cancer Therapy*, Alan R. Liss, Inc., pp. 77–96). Alternatively, a clone encoding at least the Fab portion of the antibody may be obtained by screening Fab expression libraries (e.g., as described in Huse et al., 1989, *Science* 246:1275–1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid sequence encoding at least the variable domain of the antibody is obtained, it may be introduced into a vector containing the nucleotide sequence encoding the constant regions of the antibody (see, e.g., PCT Publication No. WO 86/05807; PCT Publication No. WO 89/01036; and U.S. Pat. No. 5,122,464). Vectors containing the complete light or heavy chain that allow for the expression of a complete antibody molecule are available. Then, the nucleic acid encoding the antibody can be used to introduce the nucleotide substitutions or deletion necessary to substitute (or delete) the one or more variable region cysteine residues participating in an intrachain disulfide bond with an amino acid residue that does not contain a sulfhydryl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCT based methods, etc.

In addition, techniques developed for the production of "chimeric antibodies" (Morrison et al., 1984, Proc. Natl. Acad. Sci. 81:851–855; Neuberger et al., 1984, *Nature* 312:604–608; Takeda et al., 1985, Nature 314:452–454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, 1988, Science 242:423–42; Huston et al., 1988, Proc. Natl. Acad. Sci. USA 85:5879–5883; and Ward et al., 1989, Nature 334:544–54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli*may also be used (Skerra et al., 1988, Science 242:1038–1041).

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments.

Once a nucleic acid sequence encoding an antibody of the invention has been obtained, the vector for the production of the antibody may be produced by recombinant DNA technology using techniques well known in the art. Methods which are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, 2d Ed., Cold Spring Harbor Laboratory, Cold Spring Harbor, NY) and Ausubel et al. (eds., 1998, Current Protocols in Molecular Biology, John Wiley & Sons, NY).

An expression vector comprising the nucleotide sequence of an antibody or the nucleotide sequence of an antibody can be transferred to a host cell by conventional techniques (e.g., electroporation, liposomal transfection, and calcium phosphate precipitation) and the transfected cells are then cultured by conventional techniques to produce the antibody of the invention. In specific embodiments, the expression of the antibody is regulated by a constitutive, an inducible or a tissue, specific promoter.

The host cells used to express the recombinant antibody of the invention may be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 198, Gene 45:101; Cockett et al., 1990, Bio/Technology 8:2).

A variety of host-expression vector systems may be utilized to express the immunoglobulin molecules of the invention. Such host-expression systems represent vehicles by which the coding sequences of the antibody may be produced and subsequently purified, but also represent cells which may, when transformed or transfected with the appropriate nucleotide coding sequences, express the immunoglobulin molecule of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expres-sion vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BHK, 293, 293T, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101–3109; Van Heeke & Schuster, 1989, J. Biol. Chem. 24:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1or E3) will result in a recombinant virus that is viable and capable of expressing the immunoglobulin molecule in infected hosts. (e.g., see Logan & Shenk, 1984, Proc. Natl. Acad. Sci. USA 81:355–359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody Such engineered cell lines may be particularly useful in screening and evaluation of compounds that interact directly or indirectly with the antibody.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci.

USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIB TECH 11 (5):155–215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1; and hygro, which confers resistance to hygromycin (Santerre et al., 1984, Gene 30:147).

The expression levels of an antibody can be increased by vector amplification (for a review, see Bebbington and Hentschel, *The use of vectors based on gene amplification for the expression of cloned genes in mammalian cells in DNA cloning*, Vol.3. (Academic Press, New York, 1987)). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once the antibody has been recombinantly expressed, it may be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

5.5 Antibody Conjugates

In a preferred embodiment, anti-C3b(i) antibodies or fragments thereof are conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See generally U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{111}$In or $^{99}$TC.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In one embodiment, anti-C3b(i) antibodies are conjugated to cobra venom factor. In accordance with the invention, C3b(i) specific antibodies conjugated to cobra venom factor are utilized in vitro to deplete cancerous cells from, e.q., bone marrow obtained from an animal, preferably a mammal and most preferably a human, with cancer. Methods of conjugating antibodies to cobra venom factor are taught in U.S. Pat. No. 5,773,243, which is incorporated herein by reference in its entirety.

The conjugates of the invention can be used for modifying a given biological response; thus, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, IL-1, IL-2, IL-4, IL-5, IL-6, IL-7, Il-8, Il-9, Il-10, IL-12, IL-15, granulocyte macrophase colony stimulating factor ("GM-CSF"), granulocyte colony stimulating factor ("G-CSF"), or other growth factors.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982); each of which is incorporated herein by reference.

Alternatively, an antibody can be conjugated to a second antibody to form an antibody heteroconjugate as described by Segal in U.S. Pat. No. 4,676,980, which is incorporated herein by reference.

An antibody with or without a therapeutic moiety conjugated to it can be used as a therapeutic that is administered alone or in combination with cytotoxic factor(s) and/or cytokine(s).

5.6 Depletion of Cancerous Cells In Vitro

The invention provides for methods of depleting cancerous cells from non-cancerous tissues and/or cells in vitro (or ex vivo). In particular, the invention provides for methods of depleting cancerous cells by killing them or by separating them from non-cancerous cells. In one embodiment, anti-C3b(i) antibodies alone or in combination with plasma, are combined in vitro with tissues and/or cells obtained from an animal, preferably a mammal and most preferably a human. In another embodiment, anti-C3b(i) antibodies alone or in combination with IgG antibodies, IgM antibodies and/or one or more complement components, are combined in vitro with tissues and/or cells obtained from an animal, preferably a mammal and most preferably a human. In another embodiment, anti-C3b(i) antibodies alone or in combination with antibodies immunospecific for cancer cell antigens are combined in vitro with tissues and/or cells obtained from an animal, preferably a mammal and most preferably a human. Preferably, the tissue obtained from an animal for the in vitro depletion of cancerous cells from non-cancerous cells is bone marrow and/or peripheral blood.

In a specific embodiment, monoclonal antibodies immunospecific for C3b(i) are incubated in vitro with tissues and/or cells obtained from an animal, preferably a mammal and most preferably a human. In a preferred embodiment, the monoclonal antibodies are immunospecific for C3b(i) covalently linked to IgM or IgG antibody which is bound to the cancer cells. In another preferred embodiment, the monoclonal antibodies are immunospecific for C3b(i) covalently linked to a glycoprotein or or glycolipid on the cancer cells, CD20, Her2 or PSMA.

In a preferred embodiment, bispecific antibodies which are immunospecific for C3b(i) and an effector cell receptor or antigen are incubated in vitro with tissues and/or cells obtained from an animal, preferably a mammal and most preferably a human. In another preferred embodiment, bispecific antibodies which are immunospecific for C3b(i) and a complement component (e.g., C1q) are incubated in vitro with tissues and/or cells obtained from an animal, preferably a mammal and most preferably a human. In a particular embodiment, bispecific diabodies which are antibodies fragments immunospecific for C3b(i) and a complement component (e.g., C1q) are incubated in vitro with tissues and/or cells obtained from an animal, preferably a mammal and most preferably a human. In accordance with this embodiment, the bispecific diabodies facilitate complement mediated lysis of the cancer cells.

In accordance with the invention, the anti-C3b(i) antibodies used in the in vitro depletion of cancer cells from tissues can be conjugated to detectable substances (e.g., various enzymes, fluorescent materials, luminescent materials, bioluminescent materials, and radioactive materials) or therapeutic agents (e.g., cytostatic and cytocidal agents), which are disclosed in section 5.5. For example, anti-C3b(i) antibodies may be conjugated to cobra venom factor in order to use enhanced complement activation to lyse the cancer cells. In a specific embodiment, tissues and/or cells thus depleted of cancerous cells are administered to an animal, preferably a mammal and most preferably a human. In a preferred embodiment, the tissues and/or cells are obtained from an animal with cancer prior to treatment for cancer, and tissues and/or cells depleted of cancerous cells are administered to the animal after the treatment. In yet another preferred embodiment, the in vitro depletion of cancerous cells using anti-C3b(i) antibodies is done prior to administration of autologous bone marrow peripheral blood, or peripheral blood stem cells.

Anti-C3b(i) antibodies conjugated to detectable substances can be utilized to sort cancerous cells from non-cancerous cells by methods known to those of skill in the art. In one embodiment, cancerous cells are sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150–165). Laser excitation of fluorescent moieties in the individual particles results in a small electrical charge allowing electromagnetic separation of positive and negative particles from a mixture.

In one embodiment, cells, particularly bone marrow cells or peripheral blood stem cells, obtained from an animal, preferably a mammal and most preferably a human, are incubated with fluorescently labeled C3b(i) specific antibodies for a time sufficient to allow the labeled antibodies to bind to the cells (e.g., 10 minutes, 20 minutes, 30 minutes, 45 minutes, 60 minutes, 90 minutes, 120 minutes or more), preferably between 10 to 60 minutes. In an alternative embodiment, cells, particularly bone marrow cells or peripheral blood stem cells, obtained from an animal preferably a mammal and most preferably a human, are incubated with C3b(i) specific antibodies, the cells are washed, and the cells are incubated with a second labeled antibody that recognizes the C3b(i) specific antibodies. In accordance with these embodiments, the cells are washed and processed through the cell sorter, allowing separation of cells that bind both antibodies to be separated from hybrid cells that do not bind both antibodies. FACS sorted particles may be directly deposited into individual wells of 96-well or 384-well plates to facilitate separation.

In another embodiment, magnetic beads can be used to separate cancerous cells from non-cancerous cells. Cancerous cells may be sorted using a magnetic activated cell sorting (MACS) technique, a method for separating particles based on their ability to bind magnetic beads (0.5–100 nm diameter) (Dynal, 1995). A variety of useful modifications can be performed on the magnetic microspheres, including covalent addition of antibody which immunospecifically recognizes C3b(i). A magnetic field is then applied, to physically manipulate the selected beads. The beads are then mixed with the cells to allow binding. Cells are then passed through a magnetic field to separate out cancerous cells.

5.7 Therapeutic and Prophylactic Use of Anti-C3b(i) Antibodies

The invention provides for treatment or prevention of cancer, including, but not limited to, neoplasms, tumors, metastases, or any disease or disorder characterized by uncontrolled cell growth, by the administration of therapeutically or prophylactically effective amounts of anti-C3b(i) antibodies or nucleic acid molecules encoding said antibodies. Examples of types of cancer and proliferative disorders include, but are not limited to, leukemia (e.g., myeloblastic, promyelocytic, myelomonocytic, monocytic, erythroleukemia, chronic myelocytic (granulocytic) leukemia, and chronic lymphocytic leukemia), lymphoma (e.g., Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilms' tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. In a particular embodiment, therapeutic compounds of the invention are administered to men with prostate cancer (e.g., prostatitis, benign prostatic hypertrophy, benign prostatic hyperplasia (BPH), prostatic paraganglioma, prostate adenocarcinoma, prostatic intraepithelial neoplasia, prostato-rectal fistulas, and atypical prostatic stromal lesions). The treatment and/or prevention of cancer includes, but is not limited to, alleviating symptoms associated with cancer, the inhibition of the progression of cancer, the promotion of the regression of cancer, and the promotion of the immune response. In one embodiment, commercially available or naturally occurring anti-C3b(i) antibodies, functionally active fragments or derivatives thereof are used in the present invention.

Anti-C3b(i) antibodies may be administered alone or in combination with other types of cancer treatments (e.g., radiation therapy, chemotherapy, hormonal therapy, immunotherapy and anti-tumor agents). Examples of anti-tumor agents include, but are not limited to, cisplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol. In one embodiment, one or more anti-C3b(i) antibodies are administered to an animal, preferably a mammal and most preferably a human, after surgical resection of cancer. In another embodiment, one or more anti-C3b(i) antibodies are administered to an animal, preferably a mammal and most preferably a human, in conjugation with chemotherapy or radiotherapy. In another embodiment, one or more anti-C3b(i) antibodies are administered to an animal, preferably a mammal and most preferably a human, for the prevention or treatment of cancer prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of plasma to the animal.

In a preferred embodiment, one or more anti-C3b(i) antibodies are administered to an animal, preferably a mammal and most preferably a human, for the prevention or treatment of cancer prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of IgG antibodies, IgM antibodies and/or one or more complement components to the animal. In another preferred embodiment, one or more anti-C3b(i) antibodies are administered to an animal, preferably a mammal and most preferably a human, prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies immunospecific for one or more cancer cell antigens. In yet another preferred embodiment, one or more anti-C3b(i) antibodies are administered to an animal, preferably a mammal and most preferably a human, for the prevention or treatment of cancer prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies currently used for the treatment of cancer. Examples of such antibodies include, but are not limited to, Herceptin®, Retuxan®, OvaRex, Panorex, BEC2, IMC-C225, Vitaxin, Campath I/H, Smart MI95, LymphoCide, Smart I D10, and Oncolym.

In a specific embodiment, men with prostate cancer are administered anti-C3b(i) antibodies in conjugation with androgen ablation therapy. In another specific embodiment, non-Hodgkin's lymphoma patients are treated with Retuxan® prior to the administration of anti-C3b(i) antibodies. In certain embodiments, animals with increased risk of cancer are administered a composition of the invention. Examples of such animals include, but are not limited to, humans prone breast cancer.

The invention provides methods for the treatment or prevention of viral infections in an animal, preferably a mammal and most preferably a human, said methods comprising the administration of a therapeutically or prophylactically effective amount of anti-C3b(i) antibodies or nucleic acid molecules encoding said antibodies. Examples of viral infections which can be treated or prevented in accordance with this invention include, but are limited to, viral infections caused by retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus and cytomegalovirus), arenaviruses (e.g., lassa fever virus), paramyxoviruses (e.g., morbillivirus virus, human respiratory syncytial virus, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., Sendai virus and influenza viruses A, B and C), papovaviruses (e.g., papillomavirues), picomaviruses (e.g., rhinoviruses, enteroviruses and hepatitis A viruses), poxviruses, reoviruses (e.g., rotavirues), togaviruses (e.g., rubella virus), and rhabdoviruses (e.g., rabies virus). The treatment and/or prevention of a viral infection includes, but is not limited to, alleviating symptoms associated with said infection, the inhibition or suppression of viral replication, and the enhancement of the immune response.

Anti-C3b(i) antibodies may be administered alone or in combination with other types of anti-viral agents. Examples of anti-viral agents include, but are not limited to: cytokines (e.g., IFN-α, IFN-β, and IFN-γ); inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides); inhibitors of viral mRNA capping, such as ribavirin; inhibitors of proteases such HIV protease inhibitors (e.g., amprenavir, indinavir, nelfinavir, ritonavir, and saquinavir,); amphotericin B; castanospermine as an inhibitor of glycoprotein processing; inhibitors of neuraminidase such as influenza virus neuraminidase inhibitors (e.g., zanamivir and oseltamivir); topoisomerase I inhibitors (e.g., camptothecins and analogs thereof); amantadine and rimantadine. In one embodiment, one or more anti-C3b(i) antibodies are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of plasma to the animal.

In a preferred embodiment, one or more anti-C3b(i) antibodies are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of IgG antibodies, IgM antibodies and/or one or more complement components to the animal. In another preferred embodiment, anti-C3b(i) antibodies are administered to an animal, preferably a mammal and most preferably a human, for the prevention or treatment of a viral infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies immunospecific for one or more viral antigens. Example of antibodies immunospecific for viral antigens include, but are not limited to, Synagis®, PRO542, Ostavir, and Protovir.

The invention provides methods for the treatment or prevention of microbial infections in an animal, preferably a mammal and most preferably a human, said methods comprising the administration of a therapeutically or prophylactically effective amount of anti-C3b(i) antibodies or nucleic acid molecules encoding said antibodies. Examples of microbial infections which can be treated or prevented in accordance with this invention include, but are not limited to, yeast infections, fungal infections, protozoan infections and bacterial infections. Bacteria which cause microbial infections include, but are not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma spp., Rickettsia prowazeki, Rickettsia tsutsugumushi, Chlamydia spp*., and *Helicobacter pylori*. The treatment and/or prevention of a microbial infection includes, but is not limited to, alleviating symptoms associated with said infection, the inhibition or suppression of replication, and the enhancement of the immune response.

Anti-C3b(i) antibodies may be administered alone or in combination with other types of anti-microbial agents. Examples of anti-microbial agents include, but are not limited to: antibiotics such as penicillin, amoxicillin, ampicillin, carbenicillin, ticarcillin, piperacillin, cepalospolin, vancomycin, tetracycline, erythromycin, amphotericin B, nystatin, metroidazole, ketoconazole, and pentamidine. In one embodiment, anti-C3b(i) antibodies are administered to an animal, preferably a mammal and most preferably a human, for the prevention or treatment of a microbial infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after) or concomitantly with the administration of plasma to the animal.

In a preferred embodiment, one or more anti-C 3b(i) antibodies are administered to an animal, preferably a mammal and most preferably a human, for the prevention or treatment of a microbial infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of IgG antibodies, IgM antibodies and/or one or more complement components to the animal. In another preferred embodiment, one or more anti-C3b(i) antibodies are administered to an animal, preferably a mammal and most preferably a human, for the prevention or treatment of a microbial infection prior to (e.g., 1 minute, 15 minutes, 30 minutes, 45 minutes, 1 hour, 2 hours, 4 hours, 6 hours, 8 hours, 12 hours, 24 hours, 2 days, or 1 week before), subsequent to (e.g., 1 minute, 15 minutes, 30 minutes, 45 minutes, 1 hour, 2 hours, 4 hours, 6 hours, 8 hours, 12 hours, 24 hours, 2 days, or 1 week after), or concomitantly with the administration of antibodies immunospecific for one or more microbial antigens. Example of antibodies immunospecific for microbial antigens include, but are not limited to, antibodies immunospecific for LPS and capsular polysaccharide 5/8. In certain embodiments, animals with increased risk of a viral or bacterial infection are administered a composition of the invention. Examples of such animals include, but are not limited to, human burn patients, infants, immunocompromised or immunodeficient humans, and the elderly.

The present invention provides methods for the treatment or prevention of septic shock caused by lipopolysaccharide (LPS), an endotoxin, or a constituent of the outer cell wall of a gram negative bacteria, which can be released into the circulation. In a specific embodiment anti-C3b(i) antibodies are administered to an animal, preferably a mammal and most preferably a human, to treat or prevent septic shock. In another embodiment, anti-C3(i) antibodies are administered to an animal, preferably a mammal and most preferably in human, prior to (e.g., 15 minuted, 30 minutes, 45 minutes, 1 hour, 2 hours, 6 hours, 12 hours, or 24 hours before), subsequent to (e.g., 15 minutes, 30 minutes, 45 minutes, 1 hour, 2 hours, 6 hours, 12 hours, or 24 hours after) or concomitantly with any known technique for the treatment or prevention of septic shock in said animal.

Generally, administration of products of a species origin or species reactivity (in the case of antibodies) that is the same species as that of the patient is preferred. Thus, in a preferred embodiment, human anti-C3b(i) antibodies, derivatives, analogs, or nucleic acids, are administered to a human patient for therapy or prophylaxis.

5.7.1 Gene Therapy

The present invention provides methods for the treatment or prevention of cancer, viral infection, and microbial infection comprising administering nucleic acid molecules encoding one or more anti-C3b(i) antibodies. In a specific embodiment, nucleic acids comprising sequences encoding one or more anti-C3b(i) antibodies are administered to treat or prevent cancer, viral infection or microbial infection, by way of gene therapy. In another embodiment, nucleic acids comprising sequences encoding one or more anti-C3b(i) antibodies and one or more antibodies immunospecific for cancer antigens, are administered to treat or prevent cancer, by way of gene therapy. In another embodiment, nucleic acids comprising sequences encoding one or more anti-C3b (i) antibodies and antibodies immunospecific for viral or microbial antigens are administered to treat or prevent viral or microbial infection, by way of gene therapy. In yet another embodiment, nucleic acids comprising sequences encoding anti-C3b(i) antibodies and one or more complement components are administered to treat or prevent cancer, viral infection, or microbial infection, by way of gene therapy. Gene therapy refers to therapy performed by the administration to a subject of an expressed or expressible nucleic acid. In this embodiment of the invention, the nucleic acids produce their encoded protein that mediates a prophylactic or therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5) :155–215 Methods. commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In one aspect, a composition comprising nucleic acid sequences encoding anti-C3b(i) antibodies, one or more antibodies immunospecific for cancer antigens, viral antigens or microbial antigens, and/or one or more component components in an expression vector are administered to suitable hosts. The expression of nucleic acid sequences encoding anti-C3b(i) antibodies, antibodies immunospecific for cancer antigens, viral antigens or microbial antigens, and/or component components may be regulated by any inducible, constitutive, or tissue-specific promoter known to those of skill in the art. In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

In a particular embodiment, nucleic acid molecules encoding the coding regions of anti-C3b(i) antibodies, antibodies immunospecific for cancer antigens, viral antigens or microbial antigens, and/or component components and any other desired sequences are flanked by regions that promote homologous recombination at a desired site in the genome, thus providing for intrachromosomal expression of said coding regions (Koller and Smithies, 1989, Proc. Natl. Acad. Sci. USA 86:8932–8935; Zijlstra et al., 1989, Nature 342:435–438).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/ 20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, viral vectors are used to express nucleic acid sequences. For example, a retroviral vector can be used (see Miller et al., 1993, Meth. Enzymol. 217:581–599). These retroviral vectors have been to delete retroviral sequences that are not necessary for packaging of the viral genome and integration into host cell DNA. The nucleic acid sequences encoding the antibodies to be used in gene therapy are cloned into one or more vectors, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; Mastrangeli et al., 1993, J. Clin. Invest. 91:225–234; PCT Publication WO94/12649; and Wang, et al., 1995, Gene Therapy 2:775–783. In a preferred embodiment, adenovirus vectors are used in gene therapy.

Adeno-associated virus (AAV) has also been proposed for use in gene therapy (Walsh et al., 1993, Proc. Soc. Exp. Biol. Med. 204:289–300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes, blood cells such as T lymphocytes, B lymphocytes, monocytes, macrophages, neutrophils, eosinophils, megakanyocytes, and granulocytes, and various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding anti-C3b(i) antibodies, antibodies immunospecific for cancer antigens, viral antigens or microbial antigens, and/or component components are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, Cell 71:973–985; Rheinwald, 1980, Meth. Cell Bio. 21A:229; and Pittelkow and Scott, 1986, Mayo Clinic Proc. 61:771).

5.8 Demonstration of Therapeutic or Prophylactic Utility

The compositions of the invention are preferably tested in vitro, and then in vivo for the desired therapeutic or prophylactic activity, prior to use in humans. For example, in vitro assays to demonstrate the therapeutic or prophylactic utility of a composition include, the effect of a composition on a cell line, particularly one characteristic of a specific type of cancer, or a patient tissue sample. The effect of the composition on the cell line and/or tissue sample can be determined utilizing techniques known to those of skill in the art including, but not limited to, rosette formation assays and cell lysis assays. Test compositions can be tested for their ability to augment activated immune cells by contacting activated immune cells with a test composition or a control composition and determining the ability of the test composition to modulate the biological activity of the activated immune cells. The ability of a test composition to modulate the biological activity of activated immune cells can be assessed by detecting the expression of cytokines or antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^{3}$H-thymidine incorporation assays and trypan blue cell counts. Cytokine and antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electromobility shift assays (EMSAs). The effector function of T-cells can be measured, for example, by a $^{51}$Cr-release assay (see, e.g., Palladino et al., 1987, Cancer Res. 47:5074–5079 and Blachere et al., 1993, J. Immunotherapy 14:352–356).

Test composition can be tested for their ability to reduce tumor formation in patients (i.e., animals) suffering from cancer. Test compositions can also be tested for their ability to reduce viral load or bacterial numbers patients suffering from an infectious disease. Test compositions can also be tested for their ability to alleviate of one or more symptoms associated with cancer or an infectious disease (e.q., a viral or microbial infection). Test compositions can also be tested for their ability to decrease the time course of the infectious disease. Further, test compositions can be tested for their ability to increase the survival period of patients suffering from cancer or an infectious disease (e.q., a viral or microbial infection). Techniques known to those of skill in the art can be used to analyze or test the function of the test compositions in patients.

In various embodiments, with the invention, in vitro assays which can be used to determine whether administration of a specific composition is indicated, include in vitro cell culture assays in which a patient tissue sample is grown in culture, and exposed to or otherwise administered a composition, and the effect of such composition upon the tissue sample is observed.

Compositions for use in therapy can be tested in suitable animal model systems prior to testing in humans, including but not limited to rats, mice, chicken, cows, monkeys, rabbits, etc. For in vivo testing, prior to administration to humans, any animal model system known in the art may be used.

5.9 Therapeutic/prophylactic Administration and Composition

The invention provides methods of preventing and treating cancer, viral infection, and microbial infection by administrating to an animal (e.g., cows, pigs, horses, chickens, cats, dogs) an effective amount of a composition of the invention. Compositions of the invention include any one of the following or a combination of any of the following: one or more anti-C3b(i) antibodies, one or more antibodies immunospecific for one or more cancer antigens, one or more antibodies immunospecific for one or more viral antigens, one or more antibodies immunospecific for one or more microbial antigens, one or more complement components, nucleic acid sequences encoding one or more anti-C3b(i) antibodies, nucleic acids encoding one or more antibodies immunospecific for one or more cancer cell-antigens nucleic acids encoding one or more antibodies immunospecific for one or more viral antigens; nucleic acids encoding one or more complement components, and nucleic acids encoding one or more microbial antigens. In a preferred aspect, a composition of the invention is substantially purified (e.g., substantially free from substances that limit its effect or produce undesired side-effects).

Various delivery systems are known and can be used to administer a composition of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, the composition can be delivered in a vesicle, in particular a liposome (see Langer, 1990, Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the composition can be delivered in a controlled release, or sustained release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used in a controlled release system (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target (e.g., the brain, kidney, stomach, pancreas, and lung), thus requiring only a fraction of the systemic dose (see, e.g., Goodson, in Medical Applications of Controlled Release, supra, vol. 2, pp. 115–138 (1984)).

Other controlled release systems are discussed in the review by Langer (1990, Science 249:1527–1533).

In a specific embodiment where the composition of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

The present invention also provides pharmaceutical compositions. Such compositions comprise a prophylactically or therapeutically effective amount of one or more anti-C3b(i) antibodies, one or more antibodies immunospecific for one or more cancer antigens, one or more antibodies immunospecific for one or more viral antigens, one or more antibodies immunospecific for one or more microbial antigens, one or more complement components, or a combination thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, pharmaceutical compositions for intravenous administration are solutions in sterile isotonic aqueous buffer. Where necessary, the pharmaceutical composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a composition of the invention which will be effective in the treatment or prevention of cancer, viral infection, or microbial infection can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al., 1997, J. Acquired Immune Deficiency Syndromes and Human Retrovirology 14:193).

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.10 Diagnosis and Imaging of Cancer

Labeled antibodies, derivatives and analogs thereof, which specifically bind to C3b(i) can be used for diagnostic purposes to detect, diagnose, or monitor cancer. In a preferred embodiment, anti-C3b(i) antibodies which immunospecifically bind to C3b(i) covalently bound to IgG or IgM antibodies, or C3b(i) covalently bound to a cancer cell are used for diagnostic purposes to detect, diagnosis, or monitor cancer. In a preferred embodiment, cancer is detected in the patient. The patient is an animal, preferably a mammal and most preferably a human.

In one embodiment, diagnosis is carried out by: a) administering to an animal an effective amount of a labeled molecule which immunospecifically binds to C3b(i) or C3b (i) covalently linked to a second molecule; b) waiting for a time interval following the administering for permitting the labeled molecule to preferentially concentrate at any cancerous site in the animal (and for unbound labeled molecule to be cleared to background level); c) determining background level; and d) detecting the labeled molecule in the subject, such that detection of labeled molecule above the background level indicates the presence of cancer. In one embodiment, diagnosis is carried out by: a) administering to an animal an effective amount of a labeled molecule which immunospecifically binds to C3b(i) or C3b(i) covalently linked to a second molecule prior to, subsequent to, or concomitantly with the administration of IgG antibody, IgM antibody, plasma, one or more complement components, and/or one or more antibodies which immunospecifically bind to a cancer cell antigen; b) waiting for a time interval following the administering for permitting the labeled molecule to preferentially concentrate at any cancerous site in the animal (and for unbound labeled molecule to be cleared to background level); c) determining background level; and d) detecting the labeled molecule in the subject, such that detection of labeled molecule above the background level indicates the presence of cancer. Background level can be determined by various methods including, comparing the amount of labeled molecule detected to a standard value previously determined for a particular system.

The invention provides methods for the diagnosis or detection of cancer in an animal, said methods comprising imaging said animal at a time interval after administering to said animal an effective amount of a labeled antibody which immunospecifically binds to C3b(i) or C3b(i) covalently linked to a second molecule, said time interval being sufficient to permit the labeled antibody to preferentially concentrate at any cancerous site in said animal, wherein detection of the labeled antibody localized at the site in the subject indicates the presence of cancer. The invention also provides methods for the diagnosis or detection of cancer in an animal, said methods comprising imaging said animal at a time interval after administering to said animal an effective amount of a labeled antibody which immunospecifically binds to C3b(i) or C3b(i) covalently linked to a second molecule prior to, subsequent to, or concomitantly with the administration of IgG antibody, IgM antibody, plasma, one or more complement components, and/or one or more antibodies which immunospecifically bind to a cancer cell antigen, said time interval being sufficient to permit the labeled antibody to preferentially concentrate at any cancerous site in said animal, wherein detection of the labeled antibody localized at the site in the subject indicates the presence of cancer.

Depending on several variables, including the type of label used and the mode of administration, the time interval following the administering for permitting the labeled molecule to preferentially concentrate at any cancerous site in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the cancer is carried out by repeating the method for diagnosing the cancer, for example, one month after initial diagnosis, six months after initial diagnosis, one year after initial diagnosis, etc.

U.S. patent application Ser. No. 60/181,143, filed Feb. 8, 2000, in particular page 2 of said application, is incorporated herein by reference in its entirety.

5.10.1 Methods of Detection and Imaging

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include but are not limited to: computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

5.11 Kits

The present invention also provides kits that can be used in the above methods. In one embodiment, a kit comprises one or more antibodies immunospecific for C3b(i) or C3b(i) covalently linked to a second molecule, in one or more containers. In another embodiment, a kit comprises one or more antibodies immunospecific for C3b(i) or C3b(i) covalently linked to a second molecule and IgM antibody, in one or more containers. In another embodiment, a kit comprises one or more antibodies immunospecific for C3b (i) or C3b(i) covalently linked to a second molecule and IgG antibody, in one or more containers. In another embodiment, a kit comprises one or more antibodies immunospecific for C3b(i) or C3b(i) covalently linked to a second molecule and one or more complement components, in one or more containers. In another embodiment, a kit comprises one or more antibodies immunospecific for C3b(i) or C3b(i) covalently linked to a second molecule and one or more antibodies immunospecific for one or more cancer cell antigens, viral antigens, or microbial antigens, in one or more containers. In another embodiment, a kit comprises one or more antibodies immunospecific for C3b(i) or C3b(i) covalently linked to a second molecule, IgM or IgG antibody, and one or more complement components in one or more containers. In yet another embodiment, a kit comprises one or more antibodies immunospecific for C3b(i) or C3b(i) covalently linked to a second molecule, one or more antibodies immunospecific for one or more cancer cell antigens, viral antigens or microbial antigens, and one or more complement components, in one or more containers.

Preferably, the kits of the present invention further comprise a control antibody which is not immunospecific for C3b(i) or C3b(i) covalently linked to a second molecule. In a specific embodiment, the kits of the present invention contain a labeled C3b(i) immunospecific antibody. In a preferred embodiment, the kits of the invention contain a C3b(i) immunospecific antibody conjugated to a therapeutic agent. In another preferred embodiment, the kits of the present invention contain a C3b(i) specific antibody conjugated to a diagnostic agent. In yet another preferred embodiment, the kits of the present invention contain a purified C3b(i) immunospecific antibody. In yet another embodiment, the kits of the present invention contain anti-C3b(i) antibodies which immunospecifically bind to C3b(i) covalently bound to IgG or IgM antibody, or C3b(i) covalently bound to a cancer cell, virus, or microbe.

In certain embodiments, the kits of the invention contain instructions for the use of the antibodies for the treatment, prevention or diagnosis of cancer, viral infections, or microbial infections.

6. EXAMPLE

C3b(i) as a Tumor Specific Antigen

The following example demonstrates that after opsonization of prostate tumor cells, C3b(i) can function as a tumor-specific antigen. Antibodies specific for C3b(i) can be utilized to target tumor cells for the delivery of therapeutic or diagnostic agents, including cytotoxic, chemotherapeutic, immune-enhancing drugs, radioactive compounds, genetic material and immune effector cells.

LNCaP and lineage-derived C4-2 human prostate cancer cell lines were utilized in this example to demonstrate the use of C3b(i) as a target for immunotherapy. The LNCaP/C4-2 progression model recapitulates progression of human neoplastic prostate disease from an androgen-responsive and minimally metastatic (LNCaP cells) to an androgen-refractory (defined as being able to proliferate in castrate hosts) and highly aggressive phenotype (C4-2 subline) (Thalmann et al., 1994, Canc. Res. 54:2577–81; Chung et al., 1996, Urol. Oncol. 2:99–128; Hyytinen et al., 1997, Br. J. Canc. 75:190–5). It shares remarkable similarities with clinical human prostate cancer both in its genotypic and phenotypic changes. Furthermore, the LNCaP/C4-2 progression model has been shown to be a powerful tool for evaluating anti-prostate cancer therapeutic approaches both in vitro and in vivo (Chung et al., 1997, Acta Urol. Jap. 43:815–20), especially with regard to hormone-refractory disease, for which few effective or durable treatment options currently exist (Scher et al., 1994, Sem Oncol 21:630–56).

6.1 Materials and Methods
Cell Lines and Serum Specimens

LNCaP (American Type Culture Collection, Rockville, Md.) and C4-2 (Urocor, Oklahoma City, Okla.) human prostate cancer cell lines were maintained in T-media with 5% heat inactivated fetal bovine serum (FBS; Gibco, Grand Island, N.Y.). Cultures were maintained at 37° C. in humidified 5% $CO_2$, split and harvested at 80 to 90% confluence, and treated, if applicable, at 25% confluence. Cells were collected using either phosphate buffered saline (PBS) with 2.5 mM ethylenediiitrilotetraacetic acid (EDTA; Sigma, St. Louis, Mo.) or trypsin (Gibco, Grand Island, N.Y.) diluted 1:10 in phosphate buffered saline (PBS). Samples were then washed twice in PBS by centrifugation at 450 g for 2 minutes and resuspended at a final concentration of 0.2–1×$10^7$ cells/ml in PBS with 1% bovine serum albumin (BSA-PBS).

Serum samples were obtained with written informed consent from normal male and female volunteers (University of Virginia, Charlottesville, Va.) and from men being followed for prostate disease (University of Virginia and Eastern Virginia Medical School, Norfolk, Va.). Prostate disease patients had pathologic documentation of either benign or neoplastic prostate disease. Blood was drawn into SST gel and clot activator Vacutainer tubes (Becton Dickinson, Franklin Lakes, N.J.), held at room temperature for 30 min, and then centrifuged for 20 min at 700×g to obtain serum which was stored at −80° C.

Serum Opsonization of Tumor Cells

Harvested LNCaP and C4-2 tumor cells (1×$10^7$ cells/ml in BSA-PBS) were mixed with an equal volume of freshly thawed serum and gently shaken for 20 mm at 37° C. The opsonized cells were washed twice and brought to a final concentration of 1×$10^7$ cells/ml in BSA-PBS. Alternative opsonization procedures included addition of 10 mM EDTA to sera to block all complement activation (or use of EDTA-containing plasma), addition of 10 mM ethylene glycol tetraacetic acid (EGTA) and 5 mM Mg (Mg-EGTA) to allow only alternative pathway activation, use of purified IgM (1 mg/ml, Sigma, St. Louis, Mo.), or use of IgM-depleted serum. In this case, IgM was removed from normal human sera (NHS) by incubating 2.5 ml of serum with 1.65 ml (settled volume) anti-human IgM agarose (Sigma, St. Louis, Mo.) on ice for 1 hr with gentle shaking. The depleted serum was separated from the agarose by centrifugation at 1600×g and then stored at −80° C. ELISA determinations (not shown) demonstrated that >90% of the human IgM was specifically removed from the serum by this procedure, but the level of human IgG was reduced by less than 10%.

Monoclonal Antibodies

IgG1 mAb 7C12, 2H11, and 8E11, specific for C3b(i); IgG1 mAb HB57, specific for human 1 gM; and IgG2a mAb 7G9, specific for human complement receptor 1 (CR1), have been previously reported (Ferguson et al., 1995, Arthritis Rheum 38:190; Taylor et al., 1989, J. Immunol. 143:3626; and Tosic et al., 1989, J. Immunol. Methods 120:241) and were used in parallel with isotype-matched controls. Anti-C3b(i) mAb 3E7 (IgG1), which bound to a different epitope and was not blocked by the other anti-C3b(i) mAb, was prepared by our previously described methods (Tosic et al., 1989, J. Immunol. Methods 120:241). The specificity of mAb 3E7 for C3b(i) was confirmed by indirect flow cytometry as follows. Both mAb 3E7 and 7C12 bound to serum-opsonized pig erythrocytes, as revealed by fluorescein-isothiocyanate(FITC)-labeled anti-mouse IgG. In the presence of 5 µg/ml purified, heat-treated (56° C.) C3 (Quidel, San Diego, Calif.), binding of the mAb to opsonized pig erythrocytes was reduced by 88% and 62% respectively (results not shown). Radiolabeling of mAb with $^{125}I$ was performed by the Iodogen procedure (Edberg et al., 1988, J. Immunol. 141:4258; and Fraker et al., 1978, Biochem. Biophys. Res. Commun. 80:849). A bispecific mAb complex (a heteropolymer) was prepared by cross-linking mAb 3E7 with mAb 7G9 (Segal et al., 1995, Curr Protocol Immunol 2:131; and Taylor et al., 1997, J. Immunol. 97:842).

Serum Opsonization of Tumor Cells

Harvested LNCaP and C4-2 tumor cells (approx. 5×$10^6$ cells/ml in BSA-PBS) were mixed with an equal volume of freshly thawed serum and gently shaken for 20–30 mm at 37° C. The opsonized cells were washed twice and brought to a final concentration of 5×$10^6$ cells/ml in BSA/PBS. Alternative opsonization procedures included addition of 10 mM EDTA to sera or the use of EDTA-containing plasma to block all complement activation, addition of 10 mM [ethylenebis (oxonitrilo)]-N,N,N'N'-tetraacetic acid (EGTA) and 5 mM $Mg^{+2}$ (MgEGTA) to allow only alternative pathway activation, the use of purified IgM (1 mg/ml, Sigma, St. Louis, Mo.), or the use of IgM-depleted serum. In the latter case, IgM was removed from NHS by incubating 2.5 ml serum with 1.65 ml (settled volume) anti-(human 1 gM) linked to agarose (Sigma, St. Louis, Mo.) on ice for 1 h with gentle shaking. The depleted serum was separated from the agarose by centrifugation at 1,600 g and then stored at −80° C. Enzyme-linked immunosorbent assay determinations (not shown) demonstrated that more than 90% of the human IgM was specifically removed from the serum by this procedure, but the level of human IgG was reduced by less than 10%.

Flow Cytometry and Radioimmunoassays

Opsonized cancer cells were probed with FITC-labeled goat anti-(human IgM) Fc5µ (Pierce, Rockford, Ill.), FITC-labeled goat anti-human IgG Fc (Accurate, Westbury, N.Y.), or a cocktail of the anti-C3b(i) mAb 7C12 and 8E11 (typically 200 ng each mAb/$10^6$ cells) followed by a secondary FITC-labeled goat anti-mouse IgG (Sigma, St. Louis, Mo.). All incubations were at 37° C. for 20 min in BSA-PBS. Controls included non-opsonized cells and irrelevant isotype-matched mAb. In selected cases, cells were stained with propidium iodide (Sigma, St. Louis, Mo.) used at a final concentration of 2 μg/ml in BSA/PBS for 5 min, in the dark, on ice, to ascertain IgM or C3b-opsonization of the viable cell populations only. Viability was usually above 75%. One- or two-color fluorescence analysis was performed with CellQuest software on a FACSCalibur flow cytometer (Becton Dickinson, San Jose, Calif.).

Studies of the binding of $^{125}$I-labeled anti-C3b(i) and anti-human IgM mAb to cancer cells followed previously published procedures (Edberg et al., 1988, J. Immunol. 141:4258; and Taylor et al., 1989, J. Immunol. 143:3626). Briefly, after opsonization, $5 \times 10^6$ cancer cells were incubated for 20–30 min with $^{125}$I-labeled mAb 7C12, 8E11, 3E7, or HB57 (final concentrations between 0.1 μg/ml and 10 μg/ml) or matched-isotype controls. As a separate control for background binding, naive cancer cells were incubated with the $^{125}$I-labeled mAb. The level of binding of the mAb to the cancer cells was then determined by centrifuging the sample through oil and measuring radioactive counts in the cell pellets (Ross et al., 1985, J. Immunol. 135:2005). Alternatively, in order to determine if the anti-C3b(i) mAb could bind to cancer cells during complement opsonization, $^{125}$I-labeled mAb 3E7 or 7C12 was added directly to the incubation mixture containing cancer cells and NHS. After incubation at 37° C., the cells were spun through oil to measure mAb binding.

Rosette Experiments

Samples of 10 μl 50% suspension of human erythrocytes (approximately $5 \times 10^7$ cells) in either BSA/PBS or plasma were incubated with $2 \times 10^4$ LNCaP cells (either non-opsonized, or serum-opsonized as described above) in the presence or absence of 20 ng anti-CR1×anti-C3b(i)(7G9× 3E7) heteropolymer. After 30 min at 37° C., the cell mixtures were resuspended in BSA-PBS at a final concentration of 1% erythrocytes. Light microscopy was used to evaluate the presence and extent of erythrocyte/tumor-cell rosetting.

Immunohistochemistry

Paraffinized tissue sections with defined histopathology were deparaffinized treated with 3% hydrogen peroxide, blocked with Super Block (Scytek Laboratories, Logan, Utah), and then treated with Avidin/Biotin Block (Vector Laboratories Inc., Burlingame, Calif.). Fixed sections were incubated with 4 μg/ml anti-C3b(i) IgGImAb 7C12 and 8E11 overnight at 4° C., followed by biotinylated goat anti-mouse IgG and peroxidase-conjugated streptavidin (Biogenex Laboratories, San Ramon, Calif.). Subsequently, 3-amino-9-ethylcarbazole/$H_2O_2$ was used as the peroxidase substrate. Mouse IgG1 was used as a negative control for staining. The presence and extent of immunohistochemical staining was evaluated by light microscopy.

Magnetic Purging of Cancer Cells: Analyses by Radioimmunoassay (RIA)

Anti-C3b(i) mAb 2H11 (which recognizes the same epitope bound by mAb 7C12 (Tosic et al., 1989, J. Immunol. Methods 120:241) or mAb 3E7 was covalently coupled to amine-terminated BioMag particles (Polysciences Inc., Warrington, Pa.) following the manufacturer's instructions. Cancer cells were labeled with $^{51}$Cr (Ferguson et al., 1995, Arthritis Rheum 38:190), opsonized with an equal volume of NHS, washed three times and then subjected to the magnetic purging protocols (see below). For experiments with blood cells in serum, blood was collected into EDTA, the cells were washed three times and re-constituted into serum (or into plasma/EDTA as a control), and then $^{51}$Cr-labeled cancer cells were added. Alternatively, in certain experiments, $^{51}$Cr-labeled cancer cells (approx. 50,000 cells) were first mixed with aliquots of whole blood anti-coagulated in EDTA (complement activation is prevented) or in citrate (partially permissive for complement activation). After opsonization the samples were washed three times. More than 80% of the $^{51}$Cr label was retained by the cancer cells in all opsonization procedures.

After the opsonization steps, $^{125}$I containing $5 \times 10^4$ cancer cells corresponding to approx. 50,000 cpm were incubated with 100 μl BioMag particles containing approx. 100 μg anti-C3b(i) mAb, or a control irrelevant IgG antibody (goat anti-(mouse IgG) or sheep anti-FITC). After an incubation of 30 min on ice, the mixtures were placed in the Polysciences BioMag 15-ml separation unit, and 7 ml BSA/PBS was added to increase the volume of the separated (unbound) supernatant. This separation procedure was repeated two more times. Material bound to the magnetic particles was counted for $^{51}$Cr and, after a centrifugation step, pelleted material from the unbound supernatant (representing intact but unbound cells) was counted for $^{51}$Cr as well, in order to calculate the percentage of intact cells bound to the beads. Approximately 90%–95% of the initial input level of cell-associated $^{51}$Cr was found in either the pelleted supernatants or was directly bound to the particles.

Effects of Purging on Normal Cells: Analyses by Flow Cytometry

In order to determine the effects of purging on normal cells, the same procedures, which included opsonization, washing, and reaction with the BioMag particles, were performed on aliquots of whole blood and on blood cells reconstituted in serum. In these experiments the aliquots were not mixed with $^{51}$Cr-labeled cancer cells in order to avoid possible contamination of the flow cytometer with radioactivity. After the whole blood samples had been processed, they were assayed by flow cytometry with a number of standard markers (see below). Finally, we obtained blood samples that were enriched for CD34-positive cells from a leukophoresis of an oncology patient at the University of Virginia who was being treated with granulocyte-colony-stimulating factor in preparation for autologous stem cell transplantation. These samples were diluted into blood-type-matched whole blood from a normal individual (containing citrate or EDTA), or were added to washed blood cells reconstituted with serum, and subjected to the same opsonization and purging protocols.

After purging, unbound cellular fractions were reconstituted to the starting volumes and examined by flow cytometry following the manufacturers' directions for use of the developing reagents. The Becton Dickinson Multitest reagent (CN 340499, CD3 FITC/CD8 PE/CD45 PerCp/CD4 APC) was used to analyze for CD3/CD4- and CD3/CD8-positive lymphocytes. Light-scattering profiles of CD45-positive cells were used in the same experiment to count granulocytes. In separate experiments we measured CD34-positive cells by dual gating on CD45 (PerCp, BD 347474) and CD34 (APC, BD 340441, isotype control BD 340442). CD14 positive cells were identified by dual gating on CD45 and CD14 (FITC, Caltag, Burlingame, Calif., MHCDI401, isotype control MG2a01). In these measurements Fluor-Count Fluorospheres (Coulter, Miami, Fla., PN 2547053) were used to normalize sample volumes.

Radioimmunotherapy Cytotoxicity Studies

The cytotoxic effects of $^{131}$I-labeled anti-C3b(i) (7C12 and 8E11) mAbs on the LNCaP and C4-2 prostate cancer cell lines were evaluated as follows. $1 \times 10^6$ cells of each prostate cancer cell line were opsonized with 25% NHS (diluted in BSA-PBS) or maintained in BSA-PBS at 37° C. for 30 min. After washing twice with PBS, either 2 ug or 200 ng of $^{131}$I-labeled 7C12+8E11 or $^{131}$I-labeled irrelevant mAb (diluted in BSA-PBS) was added to each set of cells and incubated at room temperature for 30 min. The cells were washed twice with PBS, and plated in triplicate in 24-well tissue culture plates (Fisher Scientific, Pittsburgh, Pa.) in T-media+5% FBS at $3\times10^4$ cells per well. The plates were then placed in a humidified environment at 37° C. with 5% $CO_2$. A single media change was performed on day 3. On 5 (LNCaP) and 6 (C4-2) subsequent days, beginning 24 hr after mAb treatment, the triplicate wells were harvested to evaluate cell killing by comparing differences in 3-(4,5-dimethylthiazol-2-yl)-2,5-diphenyl-tetrazolium-bromide (MTT) (Sigma, St. Louis, Mo.) assay results.

6.2. Results

C3b(i) and IgM are Deposited on Prostate Cancer Cells

Figure 1B:
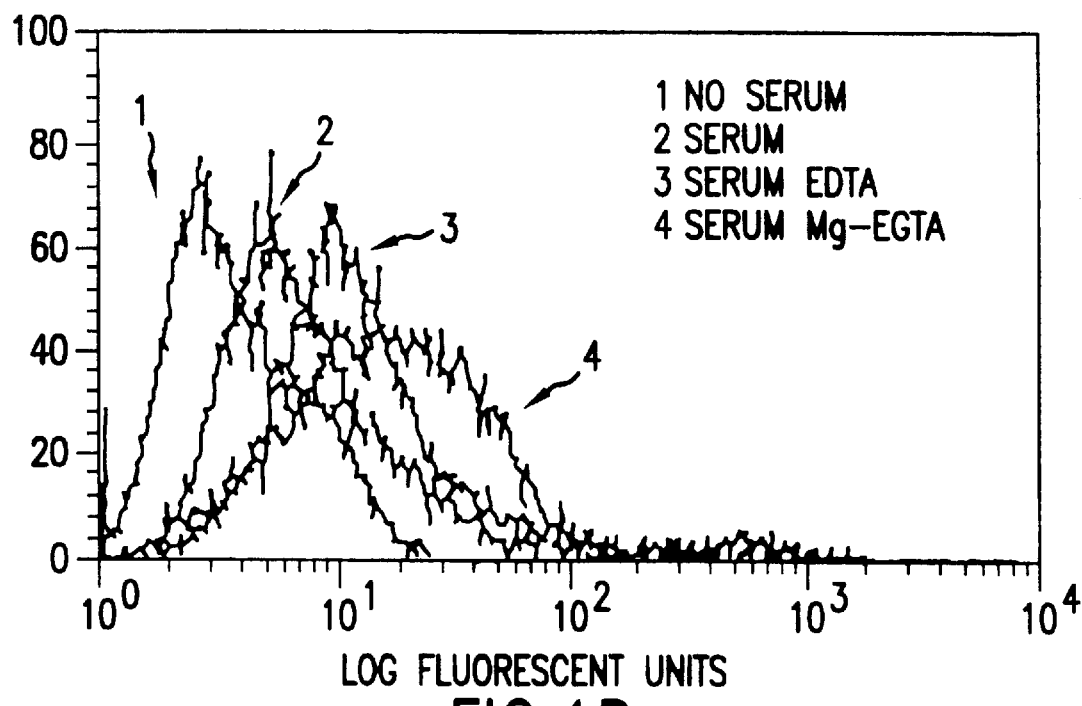
Figure 1C:
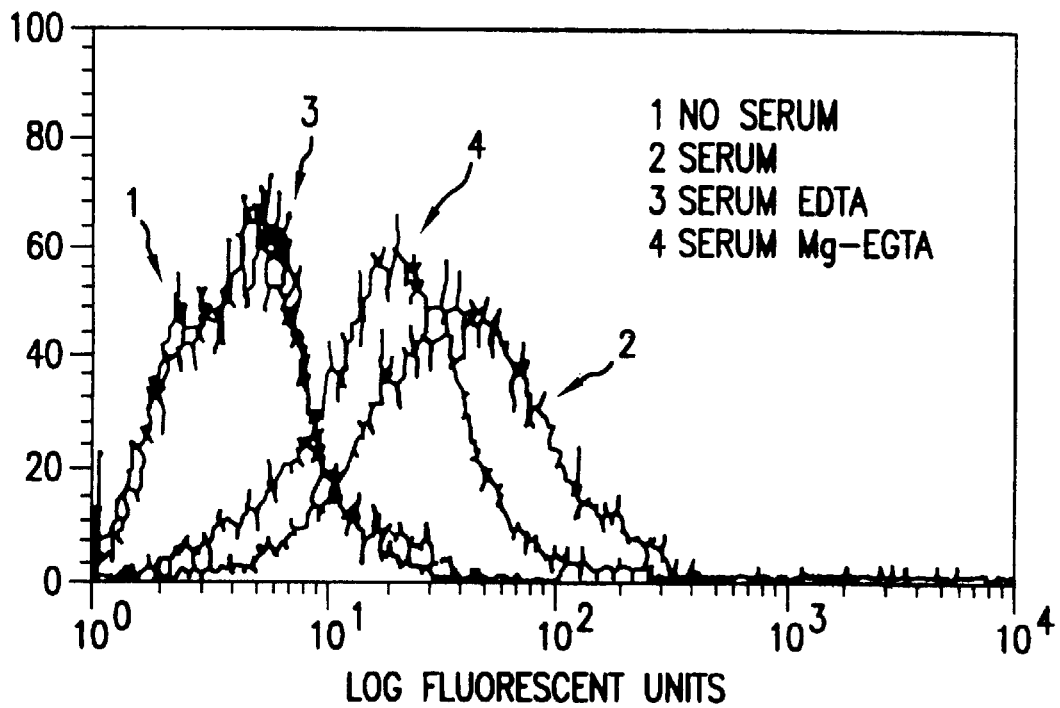
Figure 1D:
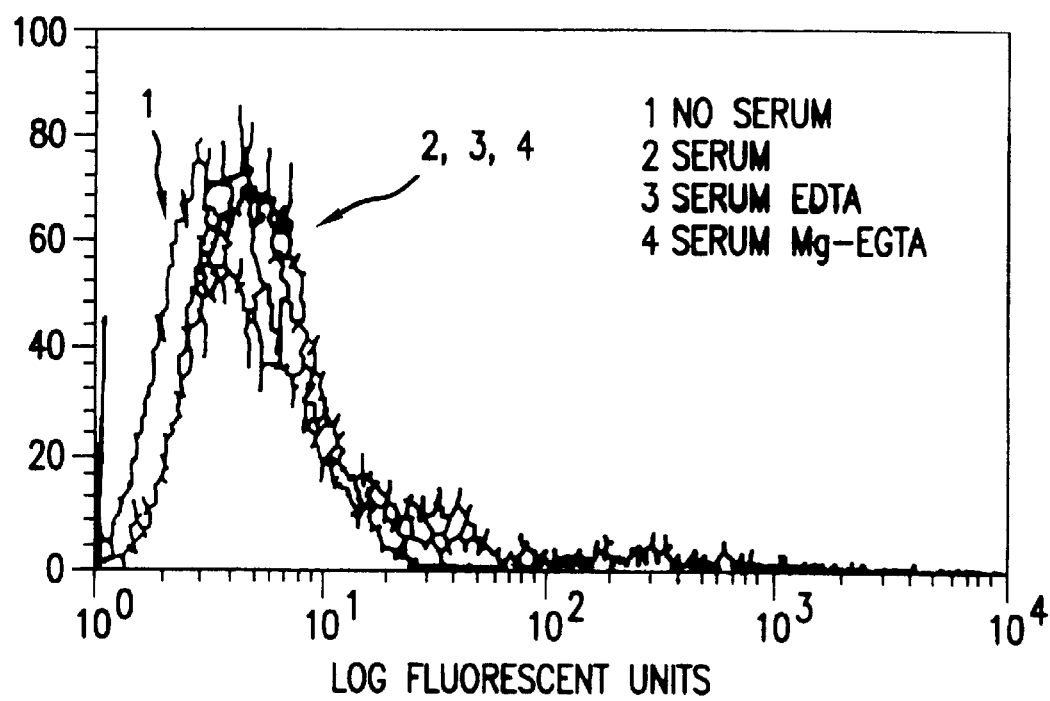

Opsonization of C4-2 prostate cancer cells (and LNCaP, see below) with normal human serum (NHS) results in deposition of substantial amounts of C3b(i) on the cells. In the representative flow-cytometry experiment displayed in FIG. 1, the effect of C3b(i) opsonization by NHS on C4-2 cells is shown in the top panel (FIG. 1A). Similar results were obtained with sera from 8 other normal individuals (data not shown). C3b(i) deposition appears to be facilitated by activation of both the classical and alternative complement pathways, but considerably less C3b(i) is demonstrable when Mg-EGTA, which allows for alternative pathway activation only, is added to the serum. Moreover, opsonization with NHS provides a source of IgM specific for the cancer cells (FIG. 1B). IgM is more readily revealed on the cancer cells when the experiment is conducted under conditions (Mg-EGTA) that block the classical pathway of complement activation, as C3b deposition via the classical pathway seems to partially block epitopes on IgM (see Table 1, below). The flow cytometry results also demonstrate that, after opsonization with serum from a prostate cancer patient, significantly less C3b(i) and IgM are deposited on the tumor cells (FIGS. 1C, D). It is noteworthy, however, that C3b(i) deposition via the alternative pathway (Mg-EGTA-treated serum) is comparable for both the normal and cancer patient serum, suggesting that the alternative pathway of complement activation remains intact in serum from prostate cancer patients.

IgM Binding Promotes Robust Cancer Cell Opsonization with C3b(i)

Figure 2B:
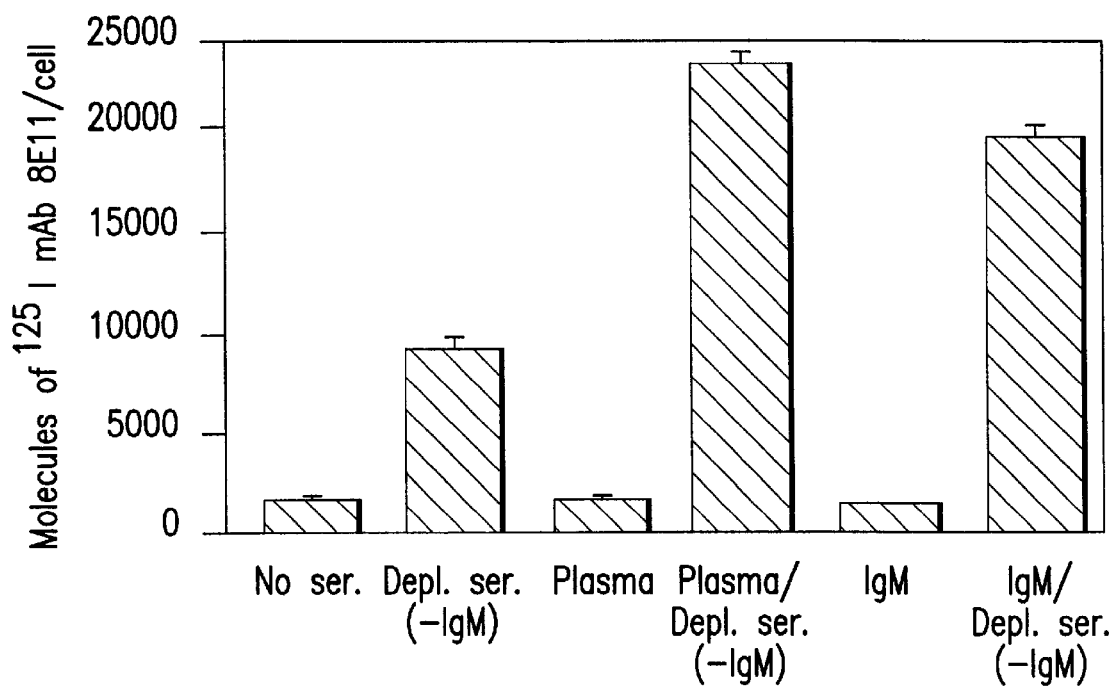

On the basis of classic studies of the mechanisms of antibody-mediated complement activation (Borsos et al., 1965, Science 150:505; Circolo et al., 1985, Mol. Immunol. 22:207; and Schreiber et al., 1972, J. Clin. Invest. 51:583), it was hypothesized that the observed complement activation on the cancer cells was predominantly facilitated by the binding of serum IgM to these cells. To isolate the effects of IgM, affinity chromatography was used to remove IgM from NHS under conditions that preserve the complement activity of the serum. Both RIA and flow cytometry demonstrate that, when IgM-depleted serum is used to opsonize LNCaP or C4-2 cells, substantially less C3b(i) is deposited on the cancer cells (FIG. 2). Normal levels of C3b(i) deposition can be restored, however, when cancer cells are first incubated with whole normal human plasma containing EDTA, which blocks both classical and alternative complement pathways. Thus, the intact plasma provides a source of human IgM sufficient to allow for robust deposition of C3b(i) on the cancer cells after they have been washed and subsequently reacted with the IgM-depleted serum, which serves as a source of complement. RIA analysis further confirms that treatment of the cancer cells with purified IgM followed by treatment with IgM-depleted serum as a complement source also results in enhanced deposition of C3b(i) on the cancer cells (FIG. 2B).

Next, the number of available epitopes on serum-opsonized cancer cells that can be targeted by anti-C3b(i) mAb was measured. Dose-response studies were performed under several conditions to estimate the number of C3b(i) sites that are generated on the cells after opsonization with NHS. The results displayed in FIG. 3 indicate that complement activation can produce in excess of 100,000 C3b(i) epitopes per cell after correction for background. It is well-known that large amounts of C3b and its breakdown products are also generated in solution during complement activation by immune complexes even if they are on cell surfaces or particulates (Circolo et al., 1984, Mol. Immunol. 21:191; Edberg et al., 1988, J. Immunol. 141 4258; and Gadd et al., 1981, Biochem J. 195:471), and it would be reasonable to anticipate that these fragments could compete for binding to the anti-C3b(i) mAb, depending upon the exact specificity of these mAb. In fact, in most experiments binding of $^{125}$I-labeled mAb 7C12 was reduced, within experimental error, to background levels when it was present during the opsonization step. For example, radioactivity bound (used to calculate molecules bound) was 6,700±100 cpm for 3 μg/ml mAb 7C12 added to the washed cells; the corresponding value for the "during" protocol was 90±100 cpm. Background labeling (no opsonization) was 900±100 cpm. However, $^{125}$I-labelled mAb 3E7 is still able to bind to the cancer cells even when it is present during the opsonization step. Moreover, in certain cases, at high input concentrations (FIG. 3B; 10 μg/ml), this mAb appears to enhance the net deposition of C3b fragments on the cancer cells. Inhibition studies (see materials and methods) with purified heat-treated C3 confirmed the specificity of mAb 3E7 for C3b(i). These findings indicate that mAb 3E7 binds preferentially to C3b(i) located on the opsonized cancer cell, and is less susceptible than mAb 7C12 to inhibition by C3b(i) fragments in the medium.

TABLE 1

C3b(i) deposition on C4-2 cells by sera from two different normal donors partially blocks the detection of human IgM by both flow cytometry and radioimmunoassay

| Treatment | Log mean flourescence intensity* | | Number of bound $^{125}$I-mAb | |
|---|---|---|---|---|
| | Anti-C3b(i) | Anti-(human IgM) | Anti-C3b(i) mAb 8E11 (mean ± SD) | Anti-human IgM) mAb HB57 (mean ± SD) |
| No serum | 7.5 | 4.7 | 1,200 ± 270 | 850 ± 30 |
| Serum | 266 | 14.8 | 27,700 ± 70 | 3,100 ± 60 |
| Serum + EDTA | 9.1 | 36.8 | 880 ± 100 | 7,900 ± 30 |
| Serum + MgEGTA | 55.6 | 29.3 | 12,000 ± 50 | 7,300 ± 330 |

*Same data presented in FIG. 1

The data strongly suggests that natural human IgM binds to surface antigens on cancer cells and facilitates activation of the classical pathway, thus allowing for deposition of large amounts of human C3b(i) on the cells. However, following complement activation and C3b(i) deposition, relatively diminished levels of cancer-cell-bound IgM can be demonstrated by flow cytometry and RIA (FIG. 1 and Table 1). This is probably due to the fact that once C3b(i) becomes covalently linked to IgM, epitopes on the IgM molecule are obstructed by C3b(i), thereby preventing the binding of anti-IgM antibodies used for flow cytometry and RIA. Deposition of C3b fragments on human IgM in immune complexes has been demonstrated in several reports (Mehta et al., 1986, J. Immunol. 136:1765; Taylor et al., 1989, J. Immunol. 143:3626; and Thornton et al., 1996, Clin. Exp. Immunol. 104:531). Therefore, some C3b(i) is complexed to the IgM on the cancer cell, and it is likely that C3b(i) is also covalently attached to glycoproteins and glycolipids on the cancer cell.

Figure 4:
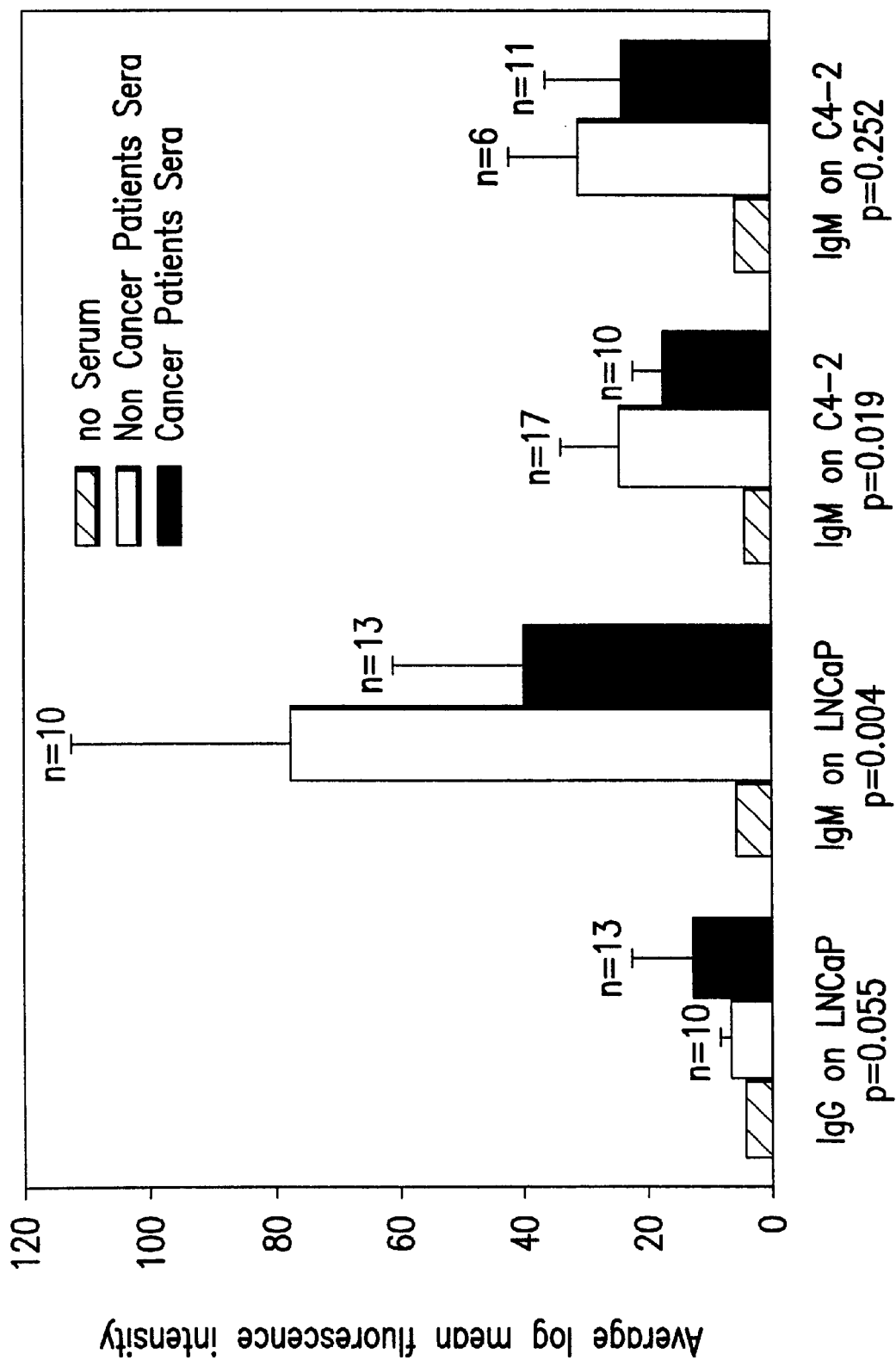

The representative data in FIG. 1 indicates that the serum from a man with prostate cancer was less effective than NHS in depositing C3b(i) on cancer cells. Several studies have previously demonstrated that the amount of IgM that can bind to cancer cells is reduced in the sera of cancer patients (Desai et al., 1995, J. Immunol. Methods 188:175; Dillman, R. O., 1994, J. Clin. Oncol. 12:1497; Gross et al., 1988, Eur. J. Cancer Clin. Oncol. 24:363; Higuchi et al., 1980, J. Clin. Lab. Immunol. 4:141; and Seegal et al., 1976, Int. Arch. Allergy Appl. Immunol. 52:205). To independently confirm these findings, sera from a number of normal individuals and men with prostate cancer were surveyed to evaluate differences in the levels of anti-tumor IgM. The experiments were conducted with sera containing 0.01 M EDTA to remove the presumed confounding and blocking effect of C3b(i) in detecting cancer-cell-bound IgM. The results, displayed in FIG. 4, indicate that in two of three experiments the level of IgM bound by cancer cells was significantly greater in normal sera than in that from prostate cancer patients. The third experiment approaches significance and might have reached it if not for the small number of samples in the control group. In one of the surveys, we assayed for cancer-cell bound IgG in addition to IgM. As shown in FIG. 4, little if any IgG in NHS is bound to the cancer cells. However, sera from some of the cancer patients show a notable titer, revealed by the large standard deviation in the patients' group. Although the numbers are too small to draw definite conclusions, these results do suggest the possibility of an active antitumor immune response in some of the cancer patients. Elevated tumor-specific IgG in patients with cancer has been previously reported (Vetvicka et al., 1997, J. Immunol. 159:599).

C3b(i) Deposition is Tumor Cell-specific

Figure 5A:
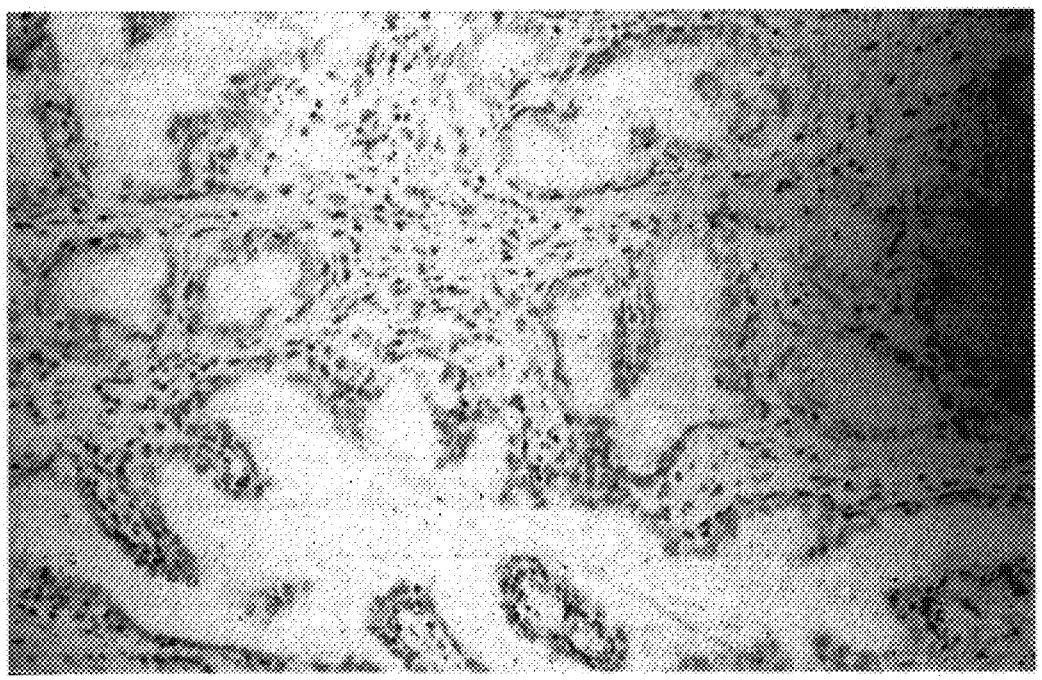
Figure 5B:
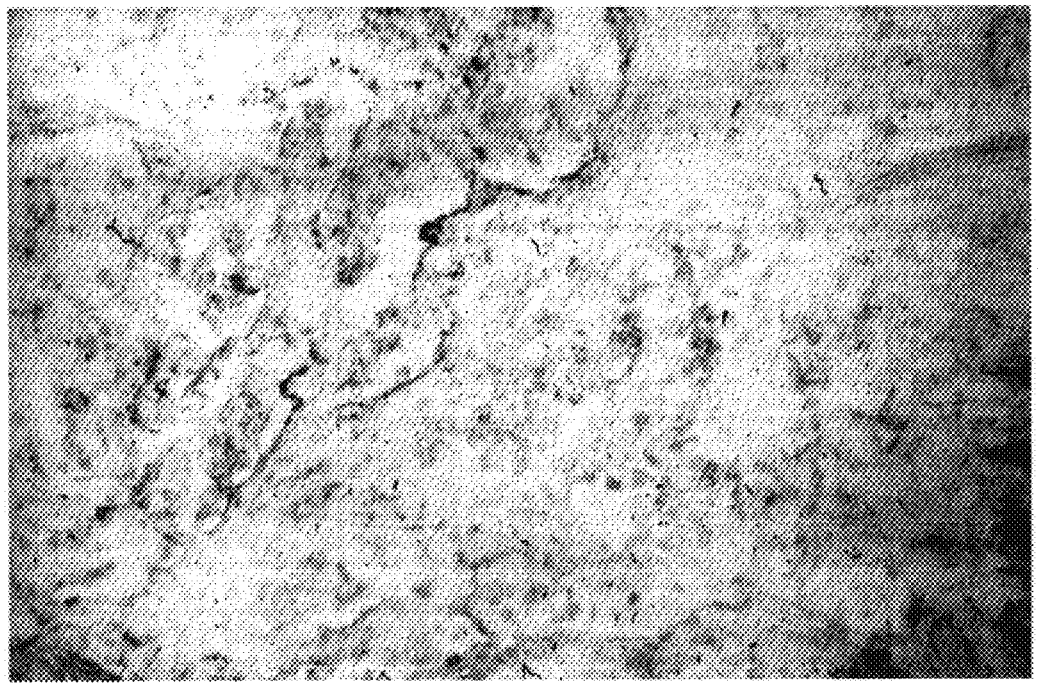

To determine the cancer-tissue specificity of the C3b(i) epitope, frozen-sectioned prostate tissue specimens with anti-C3b(i) mAb were immunohistochemically stained. The surgical specimens from 2 men undergoing transurethral resection for benign prostatic hypertrophy were used as a control. Neither control demonstrated immunohistochemical evidence of anti-C3b(i) mAb binding (FIG. 5A). Conversely, of the thirte specimens from men with prostate cancer, eight (61%) stained positively for anti-C3b(i) mAb (FIG. 5B). Furthermore, in these eight specimens, only areas of malignancy were stained; regions containing a predominance of benign cells remained negative. In only 2 specimens was staining of extremely high intensity, implying that, although complement is deposited on prostate cancer cells, inherent host complement deposition by itself provides suboptimal opsonization and systemic infusions with IgM (in the form of plasma) from normal donors may be of benefit.

Erythrocytes Rosette With Opsonized Tumor Cells in the Presence of Specific anti-CRI×anti-C3b(i) Heteropolymer One current application for mAb in cancer immunotherapy involves the generation of bispecific reagents in which a mAb specific for a cancer cell antigen is cross-linked with a mAb specific for an effector site (e.g., Fc receptors on monocytes/macrophages, granulocytes, or natural killer cells) (Renner et al., 1995, Immunol. Rev. 145:179; and Segal D M, Bakacs T, Jost C R, Kuruez I, Sconocchia G, Titus J A (1995) T-cell targeted cytotoxicity. In: Fanger M W (ed) Bispecific antibodies. Landis. Austin, Tex., p 27–42). In this approach, immunocompetent cells can be delivered directly, and specifically, to a tumor via the guidance of the anti tumor mAb. A prototype for this approach was examined by testing whether human erythrocytes could bind to C3b(i)-opsonized cancer cells through bispecific mAb complexes (heteropolymers) specific for C3b(i) and the primate erythrocyte complement receptor (CR1). As demonstrated in FIG. 6, rosettes consisting of erythrocytes completely surrounding the opsonized tumor cells are formed in normal human plasma after addition of the heteropolymer. In contrast, in the absence of anti-C3b (i)-specific heteropolymer, the majority of opsonized tumor cells bind no erythrocytes and a small percentage bind only two or three erythrocytes, because of a small amount of CR1-mediated immune adherence (not shown) (Okada et al., 1974, Nature 248:521). Finally, no rosettes were obtained if erythrocytes and heteropolymer were incubated with naive cancer cells (not shown).

Complement-opsonized Cancer Cells can be Purged by Immunomagnetic Methods

One of the more recent immunotherapeutic approaches to treatment of many forms of cancer involves the purging of cancer cells from autologous bone marrow or peripheral stem cells before autologous transplantation (Tyer et al., 1996, Clin. Cancer Res. 2:81). Although this method is not currently used as a therapy for prostate cancer, the use of prostate cancer cells is a reasonable test of the potential feasibility of using complement and anti-C3b(i) mAb to remove cancer cells selectively from solution. This approach is particularly attractive because opsonized cancer cells can be washed before addition of coupled mAb, eliminating solution-phase competition by C3b(i) fragments. As shown in Table 2, opsonization of both LNCaP and C4-2 cells with NHS followed by treatment with anti-C3b(i) mAb of different specificities bound to BioMag particles leads to very efficient binding and removal of the cancer cells. It is noteworthy that mAb 3E7, which binds to the cancer cells during serum opsonization, did not block purging with mAb 2H11 (Table 2).

TABLE 2

Removal of C3b(i) opsonized cancer cells by magnetic purging with anti-C3b(i) mAb. Results are means ± SD

| Cell type | Cells removed (%) | | Conditions |
| --- | --- | --- | --- |
| | Naive | Opsonized | |
| LNCap | 13 ± 4 | 99.0 ± 0.2 | AB⁺serum, 2H11 beads |
| C4-2 | 4 ± 2 | 98.0 ± 0.3 | AB⁺serum, 2H11 beads |
| C4-2 | 15 ± 1 | 98.0 ± 0.2 | O⁻serum, 2H11 beads |
| C4-2 | 11 ± 1 | 96.0 ± 0.1 | O⁻serum, 2H11 beads mAb 3E7 present during opsonization |
| LNCap | 18 ± 3 | 98 ± 1 | O⁺serum, 3E7 beads |
| LNCaP | 21 ± 2 | 99.0 ± 0.3 | O⁺serum, 3E7 beads 2% hematocrit[a] |
| LNCaP | 20 ± 5 | 96 ± 1 | O⁺serum, 3E7 beads 50% hematocrit[b] |

[a]Whole blood was washed three times, and the cells reconstituted to 2% hematocrit with 50% serum
[b]Whole blood was washed three times, and the cells reconstituted to 50% hematocrit with serum Robust and specific binding is demonstrable when the experiment is conducted in a reconstituted system that approximates whole blood and allows for complement activation (Table 3). When the whole-blood experiment is conducted in EDTA, which blocks complement activation, binding of the C4-2 cells to the anti-C3b(i) beads is reduced to background levels. Experiments conducted with whole blood under the two conditions that allow complement activation (serum, or citrated plasma) demonstrated a high level of binding of the C4-2 cells to the mAb 3E7 magnetic beads (Table 3). Similar experiments with reconstituted blood samples spiked with CD34-positive cells to facilitate detection by flow cytometry revealed that CD34-positive cells are not removed by the anti-C3b(i)-coated beads (3E7) after complement activation (Table 3), although there was apparently some non-specific binding of the cells to both types of bead for all conditions. Flow-cytometric analyses (Table 4) of the effect of anti-C3b magnetic bead purging on normal cells indicate no specific removal of $CD4^+$ or $CD8^+$ T lymphocytes, or granulocytes. $CD14^+$ monocytes treated with serum showed some reduction compared to controls. This reduction was not observed in citrated plasma.

Targeting drugs, toxins, and radionuclides with bispecific antibodies. In: Fanger M W, editor. Bispecific Antibodies. ed. Austin: RG Landis Co.; 1995, p. 107–20). The potential of this approach was examined by labeling anti-C3b(i) mAbs with $^{131}I$, and then testing their effectiveness in killing cancer cells in culture. After serum opsonization and reaction with the radiolabeled mAbs in solution phase (see Methods), the cells were plated. In all cases the experiments included both serum-opsonized and naive cells, as well as radiolabeled isotype-matched irrelevant mAbs. Although the level of cytotoxicity was modest, progressive killing of serum opsonized LNCaP and C4-2 cells by the $^{131}I$-labeled anti-C3b(i) mAbs over a period of 3 to 6 days was demonstrated (FIG. 7). Cell death was not observed in control cultures consisting of either nonopsonized tumor cells or $^{131}I$-labeled irrelevant mAb-treated cells. LNCaP and C4-2

TABLE 3

Effects of purging on cancer and progenitor cells in whole blood. The results for targeting of C4-2 cancer cells are based on $^{51}Cr$-labeled cells. The retention was determined by flow-cytometric analysis of samples spiked with $CD34^+$ cells. Results are means ± SD.

| Conditions | Targeting of C4-2 cancer cells: removal (%) | | Retention of $CD34^+$ cells after purging (cells/µl) | | |
|---|---|---|---|---|---|
| | 3E7 beads | IgG beads | 3E7 beads | IgG beads | No beads |
| 50% serum[a] | 98 ± 1 | 3 ± 0.3 | 6.5 ± 1 | 6.5 ± 2 | 17 ± 5 |
| 50% serum[a] | 8 ± 1 | 5 ± 0.5 | | | |
| Citrate[b] | 84 ± 8 | 9 ± 3 | 11 ± 2 | 8 ± 1 | 21 ± 1 |
| EDTA[b] | 10 ± 5 | 13 ± 3 | 8 ± 2 | 11 ± 3 | 20 ± 2 |

[a]Whole blood was washed three times, and the cells reconstituted to 50^ hematocrit with serum or plasma
[b]Whole blood anti-coagulated with citrate or EDTA

TABLE 4

Flow-cytometric analyses of the effects of purging on populations of T lymphocytes, granulocytes and monocytes. Whole blood anti-coagulated with citrate or EDTA was used or washed blood cells were reconstituted to 50% hematocrit in serum. 3E7 anti-C3b(i)-coated magnetic beads, IgG beads coated with a control irrelevant antibody.

| | Cell population (cells/µl) | | | | | | | | | | | |
|---|---|---|---|---|---|---|---|---|---|---|---|---|
| | CD3/CD4 | | | CD3/CD8 | | | Granulocytes | | | CD14 | | |
| Conditions | 3E7 | IgG | None | 3E7 | IgG | None | 3E7 | IgG | None | 3E7 | IgG | None |
| Bead: | | | | | | | | | | | | |
| 50% serum | 730 | 650 | 730 | 370 | 330 | 370 | 2,900 | 3,300 | 3,000 | 280 | 400 | 620 |
| Citrate, expt. 1 | 750 ± 60 | 660 | 900 | 380 ± 30 | 340 | 470 | 3,400 ± 500 | 3,500 | 3,500 | 500 | 530 | 540 |
| Citrate, expt. 2 | 600 | ND | 800 | 370 | ND | 560 | 2,700 | ND | 2,900 | ND | ND | ND |
| EDTA, expt. 1 | 790 | 680 | 910 | 420 | 370 | 480 | 3,000 | 3,250 | 3,300 | 370 | 410 | 580 |
| EDTA, expt. 2 | 630 | ND | 760 | 420 | ND | 490 | 3,500 | ND | 3,400 | ND | ND | ND |

By flow-cytometry experiments several other cancer cell lines, including astrocytoma (U-87 MG; ATCC), breast cancer (MDA-MB-231; ATCC), colon cancer (LoVo; ATCC), lung cancer (CCD-16Lu; ATCC), and osteosarcoma (MG-63; ATCC) were efficiently opsonized with C3b(i) by the AB-positive serum used to obtain the results shown in FIG. 1A. More than 94% of the cells registered as positive after opsonization, compared to a background level (before opsonization) of less than 5% (not shown).

Radiolabeled anti-C3b(i) mAbs can Kill Prostate Cancer Cells in Vitro

Another application of cancer-specific mAbs involves the coupling of radioactive agents to the mAbs to allow for the imaging or destruction of tumors (Glennie M J, French R R.

prostate cancer cells opsonized and treated with mAbs after being plated in tissue culture wells demonstrated similar patterns of killing (data not shown).

6.3 Discussion

It has long been recognized that C3b and its fragments can deposit on the surface of cancer cells in patients with tumors (Okada et al., 1974, Nature 248:521–25; Irie et al., 1974, Science 186:454–456.; Vetvicka et al., 1996, J. Clin. Invest. 98:50–61; Vetvicka V et al., 1997, J. Immunol. 159:599–605; and Vetvicka et al., 1999, Clin. Exp. Immunol. 115:229–35). This reaction is facilitated by natural IgM. Investigations by Springer and others suggest that the natural IgM repertoire recognizes cancer cell-associated carbohydrate epitopes which are not found on normal tissue (Hakomori et al., 1996, Canc. Res. 56:5309–18; Castronovo et al., 1989, J. Nat. Canc. Inst. 81:212–6; Springer et al., 1984, Science 224:1198–206; Springer et al., 1997, J. Mol. Med. 75;594–602; and Desai et al., 1995, J. Immunol. Methods 188:175–85). In fact, several investigators are using carbohydrate epitopes as vaccines to induce an active immune response to certain cancers (Springer, 1984, Science 224:1198–206; Springer, 1997, J. Mol. Med. 75;594–602; Livingston et al., 1997, Canc. Immunol. Immunotherapy 43 :324–30; and Zhang et al., 1998, Canc. Res. 58:2844–9). The findings presented herein demonstrate the utility of deposited C3b(i) as a tumor-associated membrane antigen with which to design a general diagnostic and therapeutic modality.

Large amounts of C3b(i) have been shown to specifically deposit on cancer cells after opsonization with NHS (FIGS. 1, 2 and 3 and Table 1). As indicated in FIGS. 1 and 4, the level of the presumably protective IgM is often reduced in cancer patients, including those with breast tumors (Desai et al., 1995, J. Immunol. Methods 188:175–85; Seegal et al., 1976, Int. Arch. Allergy App. Immunol. 52:205–11; Higuchi et al., 1980, J. Lab Chin. Immunol. 5:407–18; and Gross et al., 1988, Eur. J. Canc. Chin. Oncol. 24:363–7). Therefore, the infusion of normal human plasma in some cancer patients will help to restore or enhance C3b(i) opsonization of tumor sites accessible to the bloodstream. However, even if normal human plasma deposits a large quantity of C3b(i) on the cancer cell surface, it is unlikely that this action alone will be sufficient to eradicate a tumor, since cancer cells often express high levels of complement control proteins (Gorter et al., 1996, Lab. Invest. 74:1039–49; Maenpaa et al., 1996, Am J Path 148:1139–52; and Li et al., 1997, Int. J. Canc. 71:1049–55). For example, the expression of CD59 ("protectin") by cancer cells blocks the action of the membrane attack complex which might otherwise lyse the cancer cell. The results presented herein demonstrate that one approach to treating cancer is to infuse a patient with normal human plasma (to supply IgM and, if necessary, complement) and to then deliver systemically anti-neoplastic agents to the cancer cells by conjugating the agents to anti-C3b(i) mAbs, which would circulate through the body and home to sites of opsonized tumor cells.

To ensure that a sufficient quantity of therapeutic agent is delivered in close proximity to the tumor cell, mAb-based immunotherapy for cancer requires a very high level of selective and high avidity binding of the mAb to the tumor. The results indicate that at least 50,000 C3b(i) epitopes are available on opsonized prostate cancer cells and, based on the in vitro killing studies, this level of cancer-associated antigen should be sufficient for specific targeting of the cancer cell, enabling the delivery of abundant therapeutic or diagnositc agents.

Tumor tissue-specific delivery of therapeutic agents is crucial to avoid undesirable injury to healthy tissue. In the case of C3b(i) as a target, it is important that complement activation be limited to tumor cells. Except for a few relatively rare disease conditions (Rosse et al., 1995, Blood 86;3277–86; Morgan BP. Complement: clinical aspects and relevance to disease. ed. London: Harcourt Brace Jovanovich; 1990), the complement system is highly regulated and C3b(i) is not deposited on normal tissue. Moreover, C3b(i) deposition has been shown to be confined to areas of malignancy in human prostate tissue specimens, and is absent in benign (FIG. 5A) and hyperplastic regions (not shown). These data confirm earlier studies on breast cancer, which established a similar tumor tissue-specific pattern of opsonization (Vetvicka et al., 1997, J. Immunol. 159:599–605; Howard et al., 1979, Cancer 43:2279–87; and Niculescu et al., 1992, Am. J. Path. 140:1039–43).

Due to normal turnover, a small fraction of circulating C3 expresses antigenic epitopes similar to C3b(i), and this endogenous C3b(i)-like molecule might block the action of the anti-C3b(i) mAbs (Mollnes et al., 1987, J. Immunol. Methods 101;201–7; Petronis et al., 1998, Clin. Nuc. Med. 23:672–7). Generation of C3b fragments in the solution phase during complement activation would also tend to block binding of the mAb to cancer cells, and indeed mAb 7C12 binds to the C3b-opsonized cancer cells only after they are washed (not shown). C3b(i) covalently linked directly to IgM or to a carbohydrate on the cancer cell should, however, contain unique and specific antigenic determinants different from those expressed by C3b fragments in solution, and it should be possible to generate mAb specific for such cell-associated molecules. Indeed mAb 3E7, which was able to bind to the cancer cells during the opsonization step (FIG. 3), did not block purging with the 2H11 beads (Table 2). It is likely that other mAb can be developed that will demonstrate even greater binding specificity for C3b(i) covalently bound to the cancer cells.

The feasibility of an ex vivo application in which anti-C3b(i) mAb can be used to target and purge complement-opsonized cancer cells, which are first washed to remove potentially competing soluble C3b(i) fragments has been demonstrated (Tables 2 and 3). The procedure appears to spare normal cells including CD34-positive cells (Tables 3 and 4), which are most representative of progenitor cells (Bensinger, W. I., 1998, Bone Marrow Transplant 21:113; LaCasse et al., 1999, Blood 94:2901; and Vescio et al., 1999, Blood 93:1858). The therapeutic efficacy of purging for autologous transplantation remains controversial (Bensinger, W. I., 1998, Bone Marrow Transplant 21:113). It is reasonable to believe that contaminating cancer cells may indeed promote tumor resurgence after autologous transplantation (Schneiderman et al., 1998, Radiat Res 149:147; and Vescio et al., 1999, Blood 93:1858) and, as noted by Bensiger (1998, Bone Marrow Transplant 21:113), carefully controlled trials will be required to determine the efficacy of purging protocols. Several other new methods for purging cancer cells from bone marrow or stem cell preparations have recently been reported (LaCasse et al., 1999, Blood 94:2901; Lazzaro et al., 1995, Exp. Hematol. 23:1347; and Schneiderman et al., 1998, Radiat Res 149:147), and C3b(i) targeting may provide a powerful orthogonal approach. Use of these procedures in tandem with C3b(i)-based targeting may allow for highly efficacious purging of cancer cells from bone marrow or peripheral blood stem cells before autologous transplantation.

The potential use of anti-C3b(i) mAb in bispecific mAb complexes bound to either erythrocytes or immune effector cells (Gast et al., 1997, Cancer Immunol. Immunother. 45:121; Renner et al., 1995, Immunol. Rev. 145:179; Segal D M, Bakacs T, Jost C R, Kuruez I, Sconocchia G, Titus J A (1995) T-cell targeted cytotoxicity. In: Fanger M W (ed) Bispecific antibodies. Landis. Austin, Tex., p 27–42; and Taylor et al., 1997, Cancer Immunol. Immunother. 45:152) is illustrated by our rosetting data (FIG. 6). In the presence of the anti-C3b(i)×anti-CR1 heteropolymer, erythrocytes completely encircled prostate tumor cells opsonized with human serum. Circulating "micrometastatic" prostate tumor cells have been demonstrated in men with prostate cancer of varying grades and stages (Sokoloff et al., 1996, Cancer 77:1862). In one possible therapeutic approach, anti-C3b(i) heteropolymer constructs could be infused into men with prostate cancer in conjunction with, or soon after an infusion of normal serum, in order to target the tumor cells.

Once the tumor cells are opsonized, anti-C3b(i) mAbs coupled with toxic agents or radioisotopes can be administered to individuals. The potential use of this approach is illustrated in FIG. 7. When LNCaP and C4-2 cells were treated with $^{131}$I-labeled specific anti-C3b(i) mAbs, only those cells that had been opsonized with NHS prior to treatment with the $^{131}$I-anti-C3b(i) mAbs were killed (FIG. 7). This approach can also be utilized for diagnostic imaging purposes, similar to the PROSTASCINT™ scan, when tumor cell deposits are effectively opsonized and then targeted with anti-C3b(i) mAb-conjugated compounds (Petronis et al., 1998, Clin. Nuc. Med. 23:672–7).

The results herein demonstrate that while opsonization with normal human serum results in the deposition of large amounts of IgM and C3b(i) on prostate cancer cells, opsonization with sera from most men with prostate cancer leads to substantially diminished levels of cell-associated IgM and C3b(i). This deficiency can be restored by the infusion of normal plasma as a source of human IgM which will ultimately allow for the opsonization of cancer cells with C3b(i). These opsonized cells will therefore present unique and specific antigenic determinants for targeting by appropriate C3b(i) mAbs.

7. EXAMPLE

Effect of Antigen Specific Antibodies on the Ability of Anti-C3b(i) Antibodies to Bind to Red Blood Cells The following example demonstrates that the presence of an antibody that immunospecifically binds to a cancer antigen increases the ability of opsonized tumor cells to bind to erythrocytes in the presence of bispecific monoclonal antibody (heteropolymer) for C3b(i) and the complement receptor CR1.

Materials & Methods

In certain experiments, $^{51}$Cr-labeled Raji cells (model for B cell lymphoma) were dispersed in either serum or in serum containing 0.01 M EDTA (which blocks complement activation). They were incubated for 30 minutes at 37° C. in the presence or absence of 5 µg/ml Rituximab (Genentech, CA), to allow C3b(i) deposition. The cells were then washed three times and redispersed in normal human plasma containing human red cells at a 50 % hematocrit. In two cases the incubation mixture also contained a bispecific monoclonal antibody for C3b(i) and the complement component CR1 (HP7G9X3E7; "HP") at a concentration of 3 µg/ml. After another 30 minute incubation, 100 µl aliquots of the samples were layered on 1 ml of ficoll-hypaque and centrifuged at 500×g for 15 minutes. The $^{51}$Cr counts associated with the Raji celllls were then measured in the E pellet, and in the supernatant, which is the region in which free Raji cells are found.

In other experiments, $^{51}$Cr-labeled Raji cells were added to washed whole blood which was reconstituted in fresh serum. The samples were incubated for 30 minutes at 37° C. in the presence of varying combinations of reagents: 5 µg/ml Rituximab; 3 µg/ml HP; Rituximab plus HP incubated together; Rituximab added 15 minutes before HP; and HP added 15 minutes before Rituximab. After another 30 minute incubation, duplicate 200 µl aliquots of the samples were layered on 1 ml of ficoll-hypaque and centrifuged at 500×g for 15 minutes. The $^{51}$Cr counts associated with the Raji celllls were then measured in the E pellet, and in the supernatant, which is the region in which free Raji cells are found.

Results

As shown in FIGS. 9 and 10, a larger percentage Rajii cells bound to erythrocytes when the Rajii cells were opsonized by serum or whole blood reconstituted in serum and Rituximab in the presence of the heteropolymer than when the Rajii cells were opsonized by serum or whole blood reconstituted in serum and Rituximab in the absence of the heteropolymer. Also, a larger percentage Rajii cells bound to erythrocytes when the Rajii cells were opsonized by serum or whole blood reconstituted in serum and Rituximab in the presence of the heteropolymer than when the Rajii cells were opsonized with serum alone or whole blood reconstituted in serum alone in the presence of the heteropolymer (FIGS. 9 and 10). Further, as shown in FIG. 10, comparable numbers of Rajii cells bound to erythrocytes when the Rajii cells were opsonized with whole blood reconstituted in serum and Rituximab in presence of the heteropolymer regardless of whether the Rituximab and heteropolymer were added to the Rajii cells concomitantly or either of them was added first. Similar results were obtained with whole blood that has not been washed. These results suggest that the addition of an antibody immunospecific for a cancer cell antigen may enhance the therapeutic effect that anti-C3b(i) antibodies in cancer patients.

8. EXAMPLE

Serum-mediated Binding of Bacteria to Erythrocytes

Two gram negative bacteria, *Escherichia coli* and *Pseudomonas aeruginosa*, both of which can cause sepsis, were used to assess the ability of bacteria in the presence of serum to bind to erythrocytes. As shown in Table 2, in the presence of normal serum, these bacteria can activate complement, covalently capture C3b, and then bind to primate erythrocytes via their complement receptor 1 (CR1) which is immunospecific for C3b, the first complement activation product. Binding in sample buffers (1% BSA in phosphate buffered saline) or in serum or plasma containing EDTA (to block complement activation) averaged <15% for *E. coli*, and <12% for *P. aeruginosa*. It is important to note that only a fraction of the bacteria bind to the erythrocytes, and with time binding actually decreases (see Table 2). One possible explanation for the decrease is that C3b bound to the bacteria is converted to further breakdown products, C3bi and C3dg, and the primate erythrocyte complement receptor does not bind these ligands with any measurable affinity.

TABLE 2

Serum-Mediated Binding of Bacteria to
Erythrocytes at 37° C. is Time-Dependent

| | Percentage Bound to Erythrocytes | |
|---|---|---|
| Time, min | E. Coli | P. aeruginosa |
| 5 | 50 | 34 |
| 20 | 75 | 85 |
| 60 | 48 | 39 |
| 120 | 22 | 15 |

The mouse hybridoma cell line C3bi-E7-E7-B8 which produces the anti-C3b(i) monoclonal antibody 3E7 was deposited with the American Type Culture Collection (10801 University Boulevard, Manassas, Va. 20110-2209) on Feb. 21, 2002 and assigned Accession Number PTA-4090. This deposit will be maintained under the terms of the Budapest Treaty on the International Recognition of the Deposit of Microorganisms for the Purposes of Patent Procedure.

The present invention is not to be limited in scope by the exemplified embodiments, which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for treating or preventing cancer in an animal, said method comprising administering to the animal a therapeutically or prophylactically effective amount of one or more anti-C3b(i) antibodies.

2. A method for treating or preventing cancer in an animal, said method comprising administering to the animal a therapeutically or prophylactically effective amount of one or more anti-C3b(i) antibodies and one or more antibodies immunospecific for a cancer cell antigen.

3. The method of claim 1 or 2, wherein at least one of the anti-C3b(i) antibodies is immunospecific specific for C3b(i) linked to IgM or IgG bound to cancer cells.

4. The method of claim 1 or 2, wherein at least one of the anti-C3b(i) antibodies is immunospecific for C3b(i) linked to proteins or lipids on cancer cells.

5. The method of claim 1 or 2, wherein at least one of the anti-C3b(i) antibodies is a bispecific antibody which is immunospecific for C3b(i) and an effector cell receptor or antigen.

6. The method of claim 5 in which the effector cell is a lymphocyte, monocyte, macrophage, dendritic cell, neutrophil, natural killer cell, or erythrocyte.

7. The method of claim 6 in which the effector cell is an erythrocyte.

8. The method of claim 5 in which the receptor or antigen is CR1, CR2, CR3, CR4, CD16, CD32, CD64, or CD89.

9. The method of claim 1 or 2, wherein at least one of the anti-C3b(i) antibodies is a monoclonal antibody.

10. The method of claim 9 in which the monoclonal antibody is a human or humanized monoclonal antibody.

11. The method of claim 1 or 2 further comprising administering to the animal IgG enriched plasma.

12. The method of claim 1 or 2 further comprising administering to the animal IgM enriched plasma.

13. The method claim 1 or 2 further comprising administering to the animal one or more complement components.

14. The method of claim 2 in which at least one of the anti-C3b(i) antibodies is conjugated to a therapeutic agent.

15. The method of claim 11 further comprising administering to the animal one or more complement components.

16. The method of claim 12 further comprising administering to the animal one or more complement components.

17. The method of claim 11 further comprising administering IgM enriched plasma and one or more complement components.

18. The method of claim 2 in which at least one of the anti-C3b(i) antibodies is conjugated to a detectable agent.

19. The method of claim 1 or 2 further comprising administering to the animal plasma.

20. The method of claim 1 or 2 in which the animal is a mammal.

21. The method of claim 1 or 2 in which the animal is a human.

22. A method of treating cancer in an animal, said method comprising administering to said animal a therapeutically effective amount of an antibody immunospecific for C3b(i) covalently linked to IgM or IgG bound to cancer cells.

23. A method of treating cancer in an animal, said method comprising administering to said animal a therapeutically effective amount of an antibody immunospecific for C3b(i) covalently linked to proteins or lipids on cancer cells.

24. A method of treating cancer in an animal, said method comprising administering to said animal a therapeutically effective amount of an anti-C3b(i) antibody and an anti-CD20 antibody.

25. The method of claim 2, wherein the cancer cell antigen is CD20, HER2 or PSMA.

26. The method of claim 24, wherein the anti-C3b(i) antibody is a bispecific antibody which is immunospecific for C3b(i) and an effector cell receptor or antigen.

27. The method of claim 26 in which the effector cell is a lymphocyte, monocyte, macrophage, dendritic cell, neutrophil, natural killer cell, or erythrocyte.

28. The method of claim 27 in which the effector cell is an erythrocyte.

29. The method of claim 26 in which the antigen is CR1, CR2, CR3, CR4, CD16, CD32, CD64, or CD89.

30. The method of claim 22, 23 or 24, wherein the anti-C3b(i) antibody is a monoclonal antibody.

31. The method of claim 30 which the monoclonal antibody is a human or humanized monoclonal antibody.

32. The method of claim 22 or 23 further comprising administering to the animal IgG or IgM enriched plasma.

33. The method claim 22 or 23 further comprising administering to the animal one or more complement components.

34. The method of claim 22, 23 or 24 in which the anti-C3b(i) antibody is conjugated to a therapeutic agent.

35. The method of claim 32 further comprising administering to the animal one or more complement components.

36. The method of claim 22 or 23 further comprising administering to the animal plasma.

37. The method of claim 22, 23 or 24 in which the animal is a mammal.

38. The method of claim 37 in which the mammal is a human.

39. The method of claim 2, wherein at least one of the anti-C3b(i) antibodies is 3E7 produced by the hybridoma deposited with the ATCC as Accession No. PTA-4090.

40. The method of claim 22, 23 or 24, wherein the anti-C3b(i) antibody is 3E7 produced by the hybridoma deposited with the ATCC as Accession No. PTA-4090.

41. The method of claim 24, wherein the anti-CD20 antibody is rituximab.

42. The method of claim 24, wherein the anti-C3b(i) antibody is 3E7 produced by the hybridoma deposited with the ATCC as Accession No. PTA-4090 and the anti-CD20 antibody is rituximab.

43. The method of claim 24, wherein the anti-C3b(i) antibody is immunospecific for C3b(i) covalently linked to IgM or IgG bound to cancer cells.

44. The method of claim 24, wherein the anti-C3b(i) antibody is immunospecific for C3b(i) covalently linked to proteins or lipids in cancer cells.

45. The method of claim 22 or 23, further comprising administering to the animal one or more purified complement components.

46. The method of claim 22 or 23, further comprising administering plasma to the animal.

* * * * *